US 7,183,402 B2

(12) United States Patent
Murdin et al.

(10) Patent No.: US 7,183,402 B2
(45) Date of Patent: Feb. 27, 2007

(54) CHLAMYDIA ANTIGENS AND CORRESPONDING DNA FRAGMENTS AND USES THEREOF

(75) Inventors: Andrew D. Murdin, Richmond Hill (CA); Raymond P. Oomen, Aurora (CA); Joe Wang, Toronto (CA); Pamela Dunn, Woodbridge (CA)

(73) Assignee: Sanofi Pasteur Limited, Ontario (CA)

( * ) Notice: Subject to any disclaimer, the term of this patent is extended or adjusted under 35 U.S.C. 154(b) by 0 days.

(21) Appl. No.: 10/976,917

(22) Filed: Nov. 1, 2004

(65) Prior Publication Data

US 2005/0069942 A1    Mar. 31, 2005

Related U.S. Application Data

(63) Continuation of application No. 09/523,647, filed on Mar. 10, 2000, now abandoned.

(60) Provisional application No. 60/123,966, filed on Mar. 12, 1999.

(51) Int. Cl.
C07H 21/04 (2006.01)
C12N 15/00 (2006.01)
A01N 43/04 (2006.01)

(52) U.S. Cl. .................. 536/23.7; 435/320.1; 514/44

(58) Field of Classification Search ............ 435/320.1; 514/44; 536/23.7
See application file for complete search history.

(56) References Cited

U.S. PATENT DOCUMENTS

| | | | |
|---|---|---|---|
| 4,879,213 A | 11/1989 | Fox et al. | |
| 5,776,746 A | 7/1998 | Denney | |
| 6,020,191 A | 2/2000 | Scaria et al. | |
| 6,255,082 B1 | 7/2001 | Lizardi | |
| 6,521,745 B1 | 2/2003 | Murdin et al. | |
| 6,559,294 B1 | 5/2003 | Griffais et al. | |
| 6,693,087 B1 | 2/2004 | Murdin et al. | |
| 6,808,713 B1 | 10/2004 | Murdin et al. | |
| 6,822,071 B1 | 11/2004 | Stephens et al. | |
| 7,019,125 B2 | 3/2006 | Murdin et al. | |
| 7,070,792 B2 | 7/2006 | Murdin et al. | |
| 7,081,245 B2 | 7/2006 | Murdin et al. | |
| 2002/0082402 A1 | 6/2002 | Murdin et al. | |
| 2002/0094340 A1 | 7/2002 | Murdin et al. | |
| 2002/0094985 A1 | 7/2002 | Murdin et al. | |
| 2002/0099188 A1 | 7/2002 | Murdin et al. | |
| 2002/0132994 A1 | 9/2002 | Murdin et al. | |
| 2003/0100706 A1 | 5/2003 | Murdin et al. | |
| 2004/0254130 A1 | 12/2004 | Murdin et al. | |

FOREIGN PATENT DOCUMENTS

| WO | WO 97/46709 A | 12/1997 |
|---|---|---|
| WO | WO 98/58953 A | 12/1998 |
| WO | WO 99/28475 | 6/1999 |
| WO | WO 00/24765 | 5/2000 |
| WO | WO00/27994 | 5/2000 |
| WO | WO 00/34483 | 6/2000 |
| WO | WO 00/37494 | 6/2000 |
| WO | WO 00/46359 | 8/2000 |
| WO | WO 00/66739 | 11/2000 |
| WO | WO 01/21804 A1 | 3/2001 |
| WO | WO 01/21811 A1 | 3/2001 |
| WO | WO 01/40474 A2 | 6/2001 |
| WO | WO 01/46224 A2 | 8/2001 |
| WO | WO 01/81379 A2 | 11/2001 |
| WO | WO 01/85972 A2 | 11/2001 |
| WO | WO 02/02606 A2 | 1/2002 |
| WO | WO 02/08267 A2 | 1/2002 |

OTHER PUBLICATIONS

Grayston et al. (1995), *Journal of Infectious Diseases*, 168:1231.
Campos et al. (1995), *Investigation of Opthalmology and Visual Science*, 36:1477.
Grayston et al. (1990) *Journal of Infectious Diseases*, 161:618.
Marrie (1993), *Clinical Infectious Diseases*, 18:501.
Wang et al. (1986), *Chlamydial Infections*, Cambridge University Press, Cambridge, p. 329.
Saikku et al. (1988), *Lancet*, ii: 983.
Thom et al. (1992), *Jama*, 268:68.
Linnanmaki et al. (1993), *Circulation*, 87:1030.
Saikku et al. (1992), *Annals Internal Medicine*, 116:273.
Melnick et al. (1993), *American Journal of Medicine*, 95:499.
Shor et al. (1992, *South African Medical Journal*, 82:158.
Kuo et al. (1993), *Journal of Infectious Diseases*, 167:841.
Kuo et al. (1993), *Arteriosclerosis and Thrombosis*, 13:1501.
Campbell et al. (1995), *Journal of Infectious Diseases*, 172:585.
Chiu et al. (1997), *Circulation*, 96(7): 2144-2148.
Ramirez et al. (1996), *Annals of Internal Medicine*, 125:979.
Jackson et al. 36th *ICAAC*, Abst. K121, p. 272, Sep. 15-18, 1996, New Orleans.
Fong et al. (1997), *Journal of Clinical Microbiology*, 35:48.
Hahn et al. (1998), *Ann. Allergy Asthma Immunol.*, 80(1): 45-49.
Hahn et al. (1996), *Epidemiol. Infect.*, 117(3): 513-517.
Bjornsson et al. (1996), *Scand. J. Infect. Dis.*, 28(1): 63-69.
Hahn (1995), *J. Fam. Pract.*, 41(4): 345-351.
Allegra et al., *Eur. Respir. J.*, 7(12): 2165-2168.
Hahn et al. (1991), *JAMA*, 266(2): 225-230.
Pal et al. (1996), *Infection and Immunity*, 64: 5341.
Jones et al. (1995), *Vaccine*, 13:715.
Igietseme et al. (1993), *Regional Immunology*, 5:317.
Magee et al. (1993), *Regional Immunology*, 5: 305.

(Continued)

*Primary Examiner*—Mark Navarro
(74) *Attorney, Agent, or Firm*—Foley & Lardner LLP

(57) ABSTRACT

The present invention provides a method of nucleic acid, including DNA, immunization of a host, including humans, against disease caused by infection by a strain of *Chlamydia*, specifically *C. pneumoniae*, employing a vector containing a nucleotide sequence encoding a 60 kDa cysteine-rich membrane protein of a strain of *Chlamydia pneumoniae* and a promoter to effect expression of the 60 kDa cysteine-rich membrane protein gene in the host. Modifications are possible within the scope of this invention.

36 Claims, 9 Drawing Sheets

OTHER PUBLICATIONS

Landers et al. (1991), *Infection & Immunity*, 59:3774.
Magee et al. (1995), *Infection & Immunity*, 63:516.
Cotter et al. (1995), *Infection & Immunity*, 63:4704.
Campbell et al. (1990), *Infection & Immunity*, 58:93.
McCafferty et al. (1995), *Infection & Immunity*, 63:2387-9.
Gaydos et al. (1992), *Infection & Immunity*, 60:5319 and 5323.
Wiedmann-Al-Ahmad et al. (1997), *Clin. Diagn. Lab. Immunol.*, 6:700-704.
Hughes et al. (1992), *Infect. Immun.*, 60(9): 3497.
Dion et al. (1990), *Virology*, 179:474-477.
Snijders et al. (1991), *J. Gen. Virol.*, 72:557-565.
Langeveld et al. (1994), *Vaccine*, 12(15): 1473-1480.
Ausubel et al. (1994), *Current Protocols in Microbiology*, John Wiley and Sons.
Kunkel et al. (1985), *Proc. Natl. Acad. Sci. USA*, 82:448.
Silhavey et al. (1984), *Experiments with Gene Fusion*, Cold Spring Harbor Press.
Davis et al. (1980), *A Manual for Genetic Engineering: Advanced Bacterial Genetics*, Cold Spring Harbor Press.
Casey et al. (1977), *Nucl. Acid. Res.*, 4:1539.
Cagnon et al. (1991), *Protein Engineering*, 4(7): 843.
Takase et al. (1987), *J. Bact.*, 169:5692.
Perez Melgosa et al. (1994), *Infect. Immun.*, 62:880.
Watson et al. (1990), *Nucleic Acids Res.*, 18(7):5299-5300.
Watson et al. (1995), *Microbiology*, 141:2489.
Watson et al. (1994), *Microbiology*, 140(8): 2003-2011.
Watson et al. (1994), *Microbiology*, 32(11): 2820-2823.
Melgosa et al. (1993), *FEMS Microbiol. Lett.*, 112:199.
Campbell et al. (1990), *J. Clin. Microbiol.*, 28:1261.
Iijima et al. (1994), *J. Clin. Microbiol.*, 32:583.
Bachmaier et al. (1999), *Science*, 283:1335.
Ausubel et al. (1994), *Current Protocols in Molecular Biology*, John Wiley & Sons Inc., vol. 1.
Silhavy et al. (1994), *Experiments with Gene Fusions*, Cold Spring Harbor Laboratory Press, pp. 191-195.
Davis et al. (1980), *A Manual for Genetic Engineering: Advanced Bacterial Genetics*, Cold Spring Harbor Laboratory Press, pp. 174-176.
Plotkin et al., "Vaccines" W.B. Saunders Co. Philadelphia. 1988. p. 571.
Wagels et al. (1994), *J. Clinical Microbiology*, 140(8): 2003-2011.
U.S. Appl. No. 09/857,128, filed Sep. 20, 2001, Murdin et al.
U.S. Appl. No. 09/868,987, filed Dec. 23, 1999, Murdin et al.
U.S. Appl. No. 09/471,194, filed Dec. 23, 1999, Murdin et al.
U.S. Appl. No. 09/522,606, filed Mar. 10, 2000, Murdin et al.
U.S. Appl. No. 09/609,243, filed Jun. 30, 2000, Murdin et al.
U.S. Appl. No. 09/662,813, filed Sep. 15, 2000, Murdin et al.
U.S. Appl. No. 09/663,362, filed Sep. 15, 2000, Murdin et al.
U.S. Appl. No. 09/663,360, filed Sep. 15, 2000, Murdin et al.
U.S. Appl. No. 09/663,361, filed Sep. 15, 2000, Murdin et al.
U.S. Appl. No. 09/662,814, filed Sep. 15, 2000, Murdin et al.
U.S. Appl. No. 09/662,812, filed Sep. 15, 2000, Murdin et al.
U.S. Appl. No. 09/709,473, filed Nov. 13, 2000, Murdin et al.
U.S. Appl. No. 09/709,474, filed Nov. 13, 2000, Murdin et al.
U.S. Appl. No. 09/709,384, filed Nov. 13, 2000, Murdin et al.
U.S. Appl. No. 09/747,349, filed Dec. 22, 2000, Murdin et al.
Stephens et al., "Genome Sequence of an Obligate Intracellular Pathogen of Humans: Chlamydia Trachomatis," Oct. 23, 1998, vol. 282, Science, pp. 754-759.
Kalman et al., "Comparative Genomes of Chlamydia Pneumoniae and C. Trachomatis," *Nature Genetics*, vol. 21, Apr. 1999, pp. 385-389.
Mygind et al., "Analysis of the Humoral Immune Response to Chlamydia Outer Membrane Protein 2, " *Clinical and Diagnostic Laboratory Immunology*, vol. 5, No. 3, May 1998, pp. 313-318.
Allen et al., "An intermolecular mechanism of T cell help for the production of antibodies to the bacterial pathogen, *Chlamydia trachomatis*," *Eur. J. Immunol.*, vol. 23, 1993, pp. 1169-1172.

Figure 1. Nucleotide and amino acid sequences (SEQ ID Nos: 1 and 2) of the *C. pneumoniae* 60 kDa cysteine rich membrane protein

```
ttgatcaggt agttaggaga tgaattaatt cctgactacc ttaattcaga taataaaccc 60
aaatgttgag ggtaagagtt tacaaaacat tctacccgat ggcagaagaa aaaaataaac 120
atgcgatagg agatccct atg tcc aaa ctc atc aga cga gta gtt acg gtc    171
                    Met Ser Lys Leu Ile Arg Arg Val Val Thr Val
                     1               5                  10 ctt gcg cta acg agt atg gcg agt tgc ttt gcc agc ggg ggt ata gag    219
Leu Ala Leu Thr Ser Met Ala Ser Cys Phe Ala Ser Gly Gly Ile Glu
            15                  20                  25 gcc gct gta gca gag tct ctg att act aag atc gtc gct agt gcg gaa    267
Ala Ala Val Ala Glu Ser Leu Ile Thr Lys Ile Val Ala Ser Ala Glu
        30                  35                  40 aca aag cca gca cct gtt cct atg aca gcg aag aag gtt aga ctt gtc    315
Thr Lys Pro Ala Pro Val Pro Met Thr Ala Lys Lys Val Arg Leu Val
    45                  50                  55 cgt aga aat aaa caa cca gtt gaa caa aaa agc cgt ggt gct ttt tgt    363
Arg Arg Asn Lys Gln Pro Val Glu Gln Lys Ser Arg Gly Ala Phe Cys
60                  65                  70                  75 gat aaa gaa ttt tat ccc tgt gaa gag gga cga tgt caa cct gta gag    411
Asp Lys Glu Phe Tyr Pro Cys Glu Glu Gly Arg Cys Gln Pro Val Glu
                80                  85                  90 gct cag caa gag tct tgc tac gga aga ttg tat tct gta aaa gta aac    459
Ala Gln Gln Glu Ser Cys Tyr Gly Arg Leu Tyr Ser Val Lys Val Asn
            95                  100                 105 gat gat tgc aac gta gaa att tgc cag tcc gtt cca gaa tac gct act    507
Asp Asp Cys Asn Val Glu Ile Cys Gln Ser Val Pro Glu Tyr Ala Thr
        110                 115                 120 gta gga tct cct tac cct att gaa atc ctt gct ata ggc aaa aaa gat    555
Val Gly Ser Pro Tyr Pro Ile Glu Ile Leu Ala Ile Gly Lys Lys Asp
    125                 130                 135 tgt gtt gat gtt gtg att aca caa cag cta cct tgc gaa gct gaa ttc    603
Cys Val Asp Val Val Ile Thr Gln Gln Leu Pro Cys Glu Ala Glu Phe
140                 145                 150                 155 gta agc agt gat cca gaa aca act cct aca agt gat ggg aaa tta gtc    651
Val Ser Ser Asp Pro Glu Thr Thr Pro Thr Ser Asp Gly Lys Leu Val
                160                 165                 170 tgg aaa atc gat cgc ctg ggt gca gga gat aaa tgc aaa att act gta    699
Trp Lys Ile Asp Arg Leu Gly Ala Gly Asp Lys Cys Lys Ile Thr Val
            175                 180                 185
```

Figure 1 (cont'd)

```
tgg gta aaa cct ctt aaa gaa ggt tgc tgc ttc aca gct gct act gta    747
Trp Val Lys Pro Leu Lys Glu Gly Cys Cys Phe Thr Ala Ala Thr Val
    190             195                 200 tgt gct tgc cca gag ctc cgt tct tat act aaa tgc ggt caa cca gcc    795
Cys Ala Cys Pro Glu Leu Arg Ser Tyr Thr Lys Cys Gly Gln Pro Ala
    205             210                 215 att tgt att aag caa gaa gga cct gac tgt gct tgc cta aga tgc cct    843
Ile Cys Ile Lys Gln Glu Gly Pro Asp Cys Ala Cys Leu Arg Cys Pro
220             225                 230                 235 gta tgc tac aaa atc gaa gta gtg aac aca gga tct gct att gcc cgt    891
Val Cys Tyr Lys Ile Glu Val Val Asn Thr Gly Ser Ala Ile Ala Arg
                240                 245                 250 aac gta act gta gat aat cct gtt ccc gat ggc tat tct cat gca tct    939
Asn Val Thr Val Asp Asn Pro Val Pro Asp Gly Tyr Ser His Ala Ser
            255                 260                 265 ggt caa aga gtt ctc tct ttt aac tta gga gac atg aga cct ggc gat    987
Gly Gln Arg Val Leu Ser Phe Asn Leu Gly Asp Met Arg Pro Gly Asp
        270                 275                 280 aaa aag gta ttt aca gtt gag ttc tgc cct caa aga aga ggt caa atc   1035
Lys Lys Val Phe Thr Val Glu Phe Cys Pro Gln Arg Arg Gly Gln Ile
    285                 290                 295 act aac gtt gct act gta act tac tgc ggt gga cac aaa tgt tct gca   1083
Thr Asn Val Ala Thr Val Thr Tyr Cys Gly Gly His Lys Cys Ser Ala
300                 305                 310                 315 aat gta act aca gtt gtt aat gag cct tgt gta caa gta aat atc tct   1131
Asn Val Thr Thr Val Val Asn Glu Pro Cys Val Gln Val Asn Ile Ser
                320                 325                 330 ggt gct gat tgg tct tac gta tgt aaa cct gtg gag tac tct atc tca   1179
Gly Ala Asp Trp Ser Tyr Val Cys Lys Pro Val Glu Tyr Ser Ile Ser
            335                 340                 345 gta tcg aat cct gga gac ttg gtt ctt cat gat gtc gtg atc caa gat   1227
Val Ser Asn Pro Gly Asp Leu Val Leu His Asp Val Val Ile Gln Asp
        350                 355                 360 aca ctc cct tct ggt gtt aca gta ctc gaa gct cct ggt gga gag atc   1275
Thr Leu Pro Ser Gly Val Thr Val Leu Glu Ala Pro Gly Gly Glu Ile
    365                 370                 375 tgc tgt aat aaa gtt gtt tgg cgt att aaa gaa atg tgc cca gga gaa   1323
Cys Cys Asn Lys Val Val Trp Arg Ile Lys Glu Met Cys Pro Gly Glu
380                 385                 390                 395 acc ctc cag ttt aaa ctt gta gtg aaa gct caa gtt cct gga aga ttc   1371
Thr Leu Gln Phe Lys Leu Val Val Lys Ala Gln Val Pro Gly Arg Phe
                400                 405                 410 aca aat caa gtt gca gta act agt gag tct aac tgc gga aca tgt aca   1419
Thr Asn Gln Val Ala Val Thr Ser Glu Ser Asn Cys Gly Thr Cys Thr
            415                 420                 425
```

Figure 1 (cont'd)

```
tct tgc gca gaa aca aca aca cat tgg aaa ggt ctt gca gct acc cat    1467
Ser Cys Ala Glu Thr Thr Thr His Trp Lys Gly Leu Ala Ala Thr His
        430             435                 440 atg tgc gta tta gac aca aat gat cct atc tgt gta gga gaa aat act    1515
Met Cys Val Leu Asp Thr Asn Asp Pro Ile Cys Val Gly Glu Asn Thr
    445                 450                 455 gtc tat cgt atc tgt gta act aac cgt ggt tct gct gaa gat act aac    1563
Val Tyr Arg Ile Cys Val Thr Asn Arg Gly Ser Ala Glu Asp Thr Asn
460             465                 470                 475 gta tct tta atc ttg aag ttc tca aaa gaa ctt cag cca ata gct tct    1611
Val Ser Leu Ile Leu Lys Phe Ser Lys Glu Leu Gln Pro Ile Ala Ser
                480                 485                 490 tca ggt cca act aaa gga acg att tca ggt aat acc gtt gtt ttc gac    1659
Ser Gly Pro Thr Lys Gly Thr Ile Ser Gly Asn Thr Val Val Phe Asp
            495                 500                 505 gct tta cct aaa ctc ggt tct aag gaa tct gta gag ttt tct gtt acc    1707
Ala Leu Pro Lys Leu Gly Ser Lys Glu Ser Val Glu Phe Ser Val Thr
        510                 515                 520 ttg aaa ggt att gct ccc gga gat gct cgc ggc gaa gct att ctt tct    1755
Leu Lys Gly Ile Ala Pro Gly Asp Ala Arg Gly Glu Ala Ile Leu Ser
    525                 530                 535 tct gat aca ctg act tca cca gta tca gac aca gaa aat acc cac gtg    1803
Ser Asp Thr Leu Thr Ser Pro Val Ser Asp Thr Glu Asn Thr His Val
540                 545                 550                 555 tat taa attctaagga attatcctaa agcagagcga tattccgctc tgctttagga    1859
Tyr tagctttcaa agaagtaccg ctttagtacc ttacgtacta aagcggtttt tttgttttat 1919 aagctcttca atccaatcgt agagtttctt aatcaaagat attatttaag tttctgaaat 1979 cctaagattt attttaaaag cccatctttt taggtatgta attaaattt ttaattaagc  2039 ttttcctagt gtaacctgct tctttaggaa ctacactagg agaacggtat gtcatcaaat 2099 ctacatcccg ta                                                    2111
```

Figure 2: Restriction enzyme analysis of the the *C. pneumoniae* 60 kDa cysteine rich membrane protein.

```
PmeI         |_____!_____|
PmlI         |_____!____|
Ppu10I       |_____!_____|
PpuMI        |_____!_____|
PshBI        |!_____|
Psp124BI     |_____!_____|
Psp1406I     |_____!_____|
Psp5II       |_____!_____|
PspPPI       |_____!_____|
PvuI         |_____!_____|
PvuII        |_____!_____|
RcaI         |_____!_____|
RsaI         |_____!_!_!___!_____*!_____|
SacI         |_____!_____|
SapI         |_____!____|
Sau96I       |____!_____!_____!_____|
ScaI         |_____!_!_____|
ScrFI        |_____!_____!_____!_!!_!_____!__|
SduI         |_____!_____!_____|
SfaNI        |_____!_!_____!_____|
SfcI         |____!____!___!!_____!____!_____!_____|
SnaBI        |_____!_____!_____|
SpeI         |_____!_____|
Sse9I        |*!_____!___!___!!!_____*_____*|
SspBI        |_____!___!_____|
TaiI         |_____!_____!_!_____!_____!_!_____|
TaqI         |_____!_____!_____!_!_____!_____|
TfiI         |_____!____!_____!_____|
ThaI         |_____!_____|
TruII        |!!_____!____!_!_____!!___!_____!!!*___|
Tru9I        |!!_____!____!_!_____!!___!_____!!!*___|
TscI         |_____!_____!___!_!_!_____!___!___!_____|
TseI         |_____*_____!_____|
Tsp509I      |*!_____!___!___!!!_____*_____*|
TspEI        |*!_____!___!___!!!_____*_____*|
TspRI        |_____!_____!_____|
Tth111I      |_____!_____|
VspI         |!_____|
XhoII        |____!_____!_____!_____!_____|
XmnI         |!_____!__!_____|
Zsp2I        |_____!_____|
```

Construction of pCACRMP60

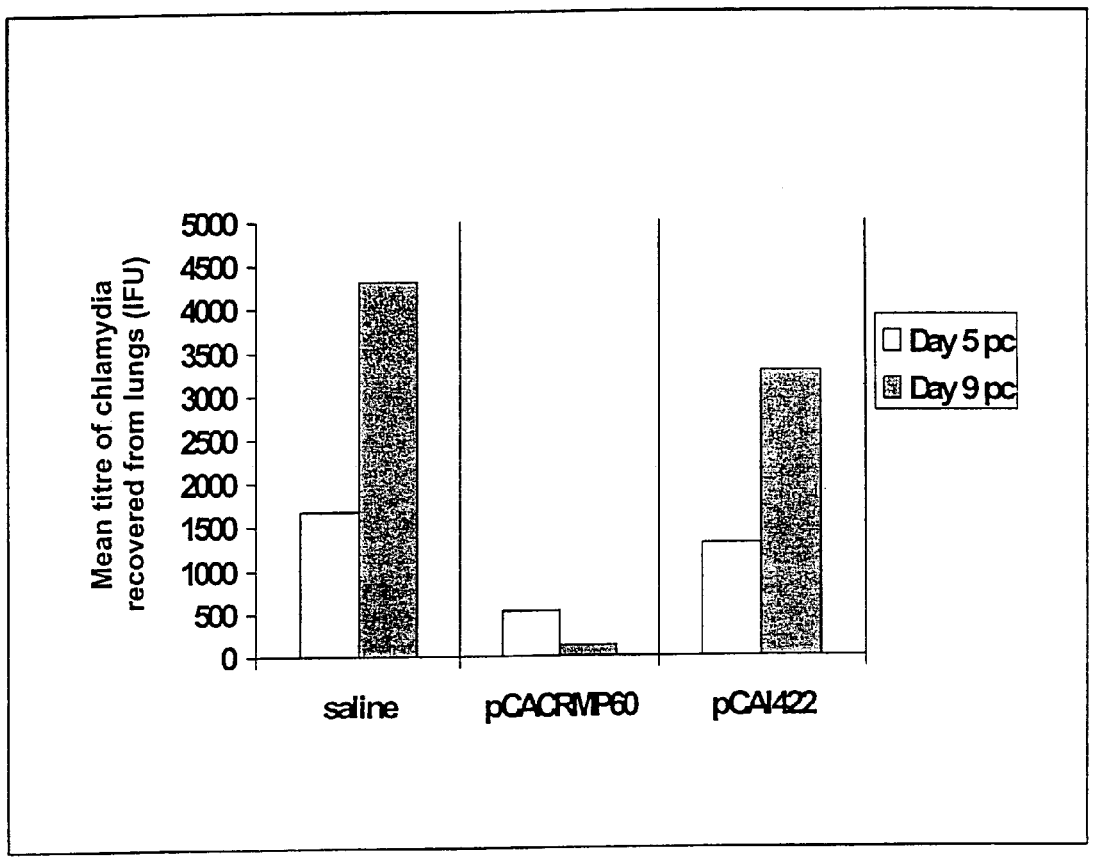
Figure 4: Protective efficacy of DNA immunization with pCACRMP60 against intranasal challenge of C. pneumoniae

SEQUENCE LISTING

<160> NUMBER OF SEQ ID NOS: 4

<210> SEQ ID NO 1
<211> LENGTH: 2111
<212> TYPE: DNA
<213> ORGANISM: Chlamydia pneumoniae
<220> FEATURE:
<221> NAME/KEY: CDS
<222> LOCATION: (139)..(1809)

<400> SEQUENCE: 1

```
ttgatcaggt agttaggaga tgaattaatt cctgactacc ttaattcaga taataaaccc      60
aaatgttgag ggtaagagtt tacaaaacat tctacccgat ggcagaagaa aaaaataaac     120
atgcgatagg agatccct atg tcc aaa ctc atc aga cga gta gtt acg gtc      171
                   Met Ser Lys Leu Ile Arg Arg Val Val Thr Val
                    1               5                  10 ctt gcg cta acg agt atg gcg agt tgc ttt gcc agc ggg ggt ata gag      219
Leu Ala Leu Thr Ser Met Ala Ser Cys Phe Ala Ser Gly Gly Ile Glu
         15                  20                  25 gcc gct gta gca gag tct ctg att act aag atc gtc gct agt gcg gaa      267
Ala Ala Val Ala Glu Ser Leu Ile Thr Lys Ile Val Ala Ser Ala Glu
     30                  35                  40
```

| | |
|---|---:|
| aca aag cca gca cct gtt cct atg aca gcg aag aag gtt aga ctt gtc<br>Thr Lys Pro Ala Pro Val Pro Met Thr Ala Lys Lys Val Arg Leu Val<br>     45                       50                    55 | 315 |
| cgt aga aat aaa caa cca gtt gaa caa aaa agc cgt ggt gct ttt tgt<br>Arg Arg Asn Lys Gln Pro Val Glu Gln Lys Ser Arg Gly Ala Phe Cys<br>60                     65                    70                    75 | 363 |
| gat aaa gaa ttt tat ccc tgt gaa gag gga cga tgt caa cct gta gag<br>Asp Lys Glu Phe Tyr Pro Cys Glu Glu Gly Arg Cys Gln Pro Val Glu<br>                     80                    85                    90 | 411 |
| gct cag caa gag tct tgc tac gga aga ttg tat tct gta aaa gta aac<br>Ala Gln Gln Glu Ser Cys Tyr Gly Arg Leu Tyr Ser Val Lys Val Asn<br>                     95                    100                  105 | 459 |
| gat gat tgc aac gta gaa att tgc cag tcc gtt cca gaa tac gct act<br>Asp Asp Cys Asn Val Glu Ile Cys Gln Ser Val Pro Glu Tyr Ala Thr<br>          110                    115                  120 | 507 |
| gta gga tct cct tac cct att gaa atc ctt gct ata ggc aaa aaa gat<br>Val Gly Ser Pro Tyr Pro Ile Glu Ile Leu Ala Ile Gly Lys Lys Asp<br>     125                    130                    135 | 555 |
| tgt gtt gat gtt gtg att aca caa cag cta cct tgc gaa gct gaa ttc<br>Cys Val Asp Val Val Ile Thr Gln Gln Leu Pro Cys Glu Ala Glu Phe<br>140                     145                    150                  155 | 603 |
| gta agc agt gat cca gaa aca act cct aca agt gat ggg aaa tta gtc<br>Val Ser Ser Asp Pro Glu Thr Thr Pro Thr Ser Asp Gly Lys Leu Val<br>                    160                    165                  170 | 651 |
| tgg aaa atc gat cgc ctg ggt gca gga gat aaa tgc aaa att act gta<br>Trp Lys Ile Asp Arg Leu Gly Ala Gly Asp Lys Cys Lys Ile Thr Val<br>               175                    180                  185 | 699 |
| tgg gta aaa cct ctt aaa gaa ggt tgc tgc ttc aca gct gct act gta<br>Trp Val Lys Pro Leu Lys Glu Gly Cys Cys Phe Thr Ala Ala Thr Val<br>          190                    195                  200 | 747 |
| tgt gct tgc cca gag ctc cgt tct tat act aaa tgc ggt caa cca gcc<br>Cys Ala Cys Pro Glu Leu Arg Ser Tyr Thr Lys Cys Gly Gln Pro Ala<br>205                     210                    215 | 795 |
| att tgt att aag caa gaa gga cct gac tgt gct tgc cta aga tgc cct<br>Ile Cys Ile Lys Gln Glu Gly Pro Asp Cys Ala Cys Leu Arg Cys Pro<br>220                     225                    230                  235 | 843 |
| gta tgc tac aaa atc gaa gta gtg aac aca gga tct gct att gcc cgt<br>Val Cys Tyr Lys Ile Glu Val Val Asn Thr Gly Ser Ala Ile Ala Arg<br>               240                    245                  250 | 891 |
| aac gta act gta gat aat cct gtt ccc gat ggc tat tct cat gca tct<br>Asn Val Thr Val Asp Asn Pro Val Pro Asp Gly Tyr Ser His Ala Ser<br>                    255                    260                  265 | 939 |
| ggt caa aga gtt ctc tct ttt aac tta gga gac atg aga cct ggc gat<br>Gly Gln Arg Val Leu Ser Phe Asn Leu Gly Asp Met Arg Pro Gly Asp<br>          270                    275                  280 | 987 |
| aaa aag gta ttt aca gtt gag ttc tgc cct caa aga aga ggt caa atc<br>Lys Lys Val Phe Thr Val Glu Phe Cys Pro Gln Arg Arg Gly Gln Ile<br>285                     290                    295 | 1035 |
| act aac gtt gct act gta act tac tgc ggt gga cac aaa tgt tct gca<br>Thr Asn Val Ala Thr Val Thr Tyr Cys Gly Gly His Lys Cys Ser Ala<br>300                     305                    310                  315 | 1083 |
| aat gta act aca gtt gtt aat gag cct tgt gta caa gta aat atc tct<br>Asn Val Thr Thr Val Val Asn Glu Pro Cys Val Gln Val Asn Ile Ser<br>               320                    325                  330 | 1131 |
| ggt gct gat tgg tct tac gta tgt aaa cct gtg gag tac tct atc tca<br>Gly Ala Asp Trp Ser Tyr Val Cys Lys Pro Val Glu Tyr Ser Ile Ser<br>                    335                    340                  345 | 1179 |
| gta tcg aat cct gga gac ttg gtt ctt cat gat gtc gtg atc caa gat<br>Val Ser Asn Pro Gly Asp Leu Val Leu His Asp Val Val Ile Gln Asp<br>     350                    355                    360 | 1227 |

-continued

```
aca ctc cct tct ggt gtt aca gta ctc gaa gct cct ggt gga gag atc      1275
Thr Leu Pro Ser Gly Val Thr Val Leu Glu Ala Pro Gly Gly Glu Ile
    365                 370                 375 tgc tgt aat aaa gtt gtt tgg cgt att aaa gaa atg tgc cca gga gaa      1323
Cys Cys Asn Lys Val Val Trp Arg Ile Lys Glu Met Cys Pro Gly Glu
380                 385                 390                 395 acc ctc cag ttt aaa ctt gta gtg aaa gct caa gtt cct gga aga ttc      1371
Thr Leu Gln Phe Lys Leu Val Val Lys Ala Gln Val Pro Gly Arg Phe
                400                 405                 410 aca aat caa gtt gca gta act agt gag tct aac tgc gga aca tgt aca      1419
Thr Asn Gln Val Ala Val Thr Ser Glu Ser Asn Cys Gly Thr Cys Thr
            415                 420                 425 tct tgc gca gaa aca aca aca cat tgg aaa ggt ctt gca gct acc cat      1467
Ser Cys Ala Glu Thr Thr Thr His Trp Lys Gly Leu Ala Ala Thr His
        430                 435                 440 atg tgc gta tta gac aca aat gat cct atc tgt gta gga gaa aat act      1515
Met Cys Val Leu Asp Thr Asn Asp Pro Ile Cys Val Gly Glu Asn Thr
    445                 450                 455 gtc tat cgt atc tgt gta act aac cgt ggt tct gct gaa gat act aac      1563
Val Tyr Arg Ile Cys Val Thr Asn Arg Gly Ser Ala Glu Asp Thr Asn
460                 465                 470                 475 gta tct tta atc ttg aag ttc tca aaa gaa ctt cag cca ata gct tct      1611
Val Ser Leu Ile Leu Lys Phe Ser Lys Glu Leu Gln Pro Ile Ala Ser
                480                 485                 490 tca ggt cca act aaa gga acg att tca ggt aat acc gtt gtt ttc gac      1659
Ser Gly Pro Thr Lys Gly Thr Ile Ser Gly Asn Thr Val Val Phe Asp
            495                 500                 505 gct tta cct aaa ctc ggt tct aag gaa tct gta gag ttt tct gtt acc      1707
Ala Leu Pro Lys Leu Gly Ser Lys Glu Ser Val Glu Phe Ser Val Thr
        510                 515                 520 ttg aaa ggt att gct ccc gga gat gct cgc ggc gaa gct att ctt tct      1755
Leu Lys Gly Ile Ala Pro Gly Asp Ala Arg Gly Glu Ala Ile Leu Ser
    525                 530                 535 tct gat aca ctg act tca cca gta tca gac aca gaa aat acc cac gtg      1803
Ser Asp Thr Leu Thr Ser Pro Val Ser Asp Thr Glu Asn Thr His Val
540                 545                 550                 555 tat taa attctaagga attatcctaa agcagagcga tattccgctc tgctttagga       1859
Tyr tagctttcaa agaagtaccg ctttagtacc ttacgtacta aagcggtttt tttgttttat    1919
aagctcttca atccaatcgt agagtttctt aatcaaagat attatttaag tttctgaaat    1979
cctaagattt attttaaaag cccatctttt taggtatgta attaaaattt ttaattaagc    2039
ttttcctagt gtaacctgct tctttaggaa ctacactagg agaacggtat gtcatcaaat    2099
ctacatcccg ta                                                        2111

<210> SEQ ID NO 2
<211> LENGTH: 556
<212> TYPE: PRT
<213> ORGANISM: Chlamydia pneumoniae

<400> SEQUENCE: 2

Met Ser Lys Leu Ile Arg Arg Val Val Thr Val Leu Ala Leu Thr Ser
  1               5                  10                  15

Met Ala Ser Cys Phe Ala Ser Gly Gly Ile Glu Ala Ala Val Ala Glu
             20                  25                  30

Ser Leu Ile Thr Lys Ile Val Ala Ser Ala Glu Thr Lys Pro Ala Pro
         35                  40                  45
```

-continued

```
Val Pro Met Thr Ala Lys Lys Val Arg Leu Val Arg Arg Asn Lys Gln
    50                  55                  60

Pro Val Glu Gln Lys Ser Arg Gly Ala Phe Cys Asp Lys Glu Phe Tyr
65                  70                  75                  80

Pro Cys Glu Glu Gly Arg Cys Gln Pro Val Glu Ala Gln Gln Glu Ser
                85                  90                  95

Cys Tyr Gly Arg Leu Tyr Ser Val Lys Val Asn Asp Cys Asn Val
                100                 105                 110

Glu Ile Cys Gln Ser Val Pro Glu Tyr Ala Thr Val Gly Ser Pro Tyr
                115                 120                 125

Pro Ile Glu Ile Leu Ala Ile Gly Lys Lys Asp Cys Val Asp Val Val
        130                 135                 140

Ile Thr Gln Gln Leu Pro Cys Glu Ala Glu Phe Val Ser Ser Asp Pro
145                 150                 155                 160

Glu Thr Thr Pro Thr Ser Asp Gly Lys Leu Val Trp Lys Ile Asp Arg
                165                 170                 175

Leu Gly Ala Gly Asp Lys Cys Lys Ile Thr Val Trp Val Lys Pro Leu
                180                 185                 190

Lys Glu Gly Cys Cys Phe Thr Ala Ala Thr Val Cys Ala Cys Pro Glu
                195                 200                 205

Leu Arg Ser Tyr Thr Lys Cys Gly Gln Pro Ala Ile Cys Ile Lys Gln
        210                 215                 220

Glu Gly Pro Asp Cys Ala Cys Leu Arg Cys Pro Val Cys Tyr Lys Ile
225                 230                 235                 240

Glu Val Val Asn Thr Gly Ser Ala Ile Ala Arg Asn Val Thr Val Asp
                245                 250                 255

Asn Pro Val Pro Asp Gly Tyr Ser His Ala Ser Gly Gln Arg Val Leu
                260                 265                 270

Ser Phe Asn Leu Gly Asp Met Arg Pro Gly Asp Lys Lys Val Phe Thr
        275                 280                 285

Val Glu Phe Cys Pro Gln Arg Arg Gly Gln Ile Thr Asn Val Ala Thr
290                 295                 300

Val Thr Tyr Cys Gly Gly His Lys Cys Ser Ala Asn Val Thr Thr Val
305                 310                 315                 320

Val Asn Glu Pro Cys Val Gln Val Asn Ile Ser Gly Ala Asp Trp Ser
                325                 330                 335

Tyr Val Cys Lys Pro Val Glu Tyr Ser Ile Ser Val Ser Asn Pro Gly
                340                 345                 350

Asp Leu Val Leu His Asp Val Val Ile Gln Asp Thr Leu Pro Ser Gly
        355                 360                 365

Val Thr Val Leu Glu Ala Pro Gly Gly Glu Ile Cys Cys Asn Lys Val
        370                 375                 380

Val Trp Arg Ile Lys Glu Met Cys Pro Gly Glu Thr Leu Gln Phe Lys
385                 390                 395                 400

Leu Val Val Lys Ala Gln Val Pro Gly Arg Phe Thr Asn Gln Val Ala
                405                 410                 415

Val Thr Ser Glu Ser Asn Cys Gly Thr Cys Thr Ser Cys Ala Glu Thr
                420                 425                 430

Thr Thr His Trp Lys Gly Leu Ala Ala Thr His Met Cys Val Leu Asp
        435                 440                 445

Thr Asn Asp Pro Ile Cys Val Gly Glu Asn Thr Val Tyr Arg Ile Cys
450                 455                 460
```

```
                                    -continued

Val Thr Asn Arg Gly Ser Ala Glu Asp Thr Asn Val Ser Leu Ile Leu
465                 470                 475                 480

Lys Phe Ser Lys Glu Leu Gln Pro Ile Ala Ser Ser Gly Pro Thr Lys
                485                 490                 495

Gly Thr Ile Ser Gly Asn Thr Val Val Phe Asp Ala Leu Pro Lys Leu
            500                 505                 510

Gly Ser Lys Glu Ser Val Glu Phe Ser Val Thr Leu Lys Gly Ile Ala
        515                 520                 525

Pro Gly Asp Ala Arg Gly Glu Ala Ile Leu Ser Ser Asp Thr Leu Thr
    530                 535                 540

Ser Pro Val Ser Asp Thr Glu Asn Thr His Val Tyr
545                 550                 555

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 3
ataagaatgc ggccgccacc atgtccaaac tcatcagacg agtag             45

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 4
gcgccggatc cgatacacgt gggtattttc tgtg                         34
```

CHLAMYDIA ANTIGENS AND CORRESPONDING DNA FRAGMENTS AND USES THEREOF

REFERENCE TO RELATED APPLICATIONS

This is a continuation of U.S. patent application Ser. No. 09/523,647 filed Mar. 10, 2000, now abandoned, which claims the benefit of U.S. Provisional Application No. 60/123,966, filed Mar. 12, 1999, the content of which is herein incorporated by reference.

FIELD OF INVENTION

The present invention relates to the *Chlamydia* 60 kDa cysteine-rich membrane protein and corresponding DNA molecules, which can be used to prevent and treat *Chlamydia* infection in mammals, such as humans.

BACKGROUND OF THE INVENTION

*Chlamydiae* are prokaryotes. They exhibit morphologic and structural similarities to gram-negative bacteria including a trilaminar outer membrane, which contains lipopolysaccharide and several membrane proteins that are structurally and functionally analogous to proteins found in *E coli*. They are obligate intra-cellular parasites with a unique biphasic life cycle consisting of a metabolically inactive but infectious extracellular stage and a replicating but non-infectious intracellular stage. The replicative stage of the life-cycle takes place within a membrane-bound inclusion which sequesters the bacteria away from the cytoplasm of the infected host cell.

*C. pneumoniae* is a common human pathogen, originally described as the TWAR strain of *Chlamydia psittaci* but subsequently recognised to be a new species. *C. pneumoniae* is antigenically, genetically and morphologically distinct from other chlamydia species (*C. trachomatis, C. pecorum* and *C. psittaci*). It shows 10% or less DNA sequence homology with either of *C. trachomatis* or *C. psittaci*.

*C. pneumoniae* is a common cause of community acquired pneumonia, only less frequent than *Streptococcus pneumoniae* and *Mycoplasma pneumoniae* (Grayston et al. (1995) Journal of Infectious Diseases 168:1231; Campos et al. (1995). Investigation of Ophthalmology and Visual Science 36:1477). It can also cause upper respiratory tract symptoms and disease, including bronchitis and sinusitis (Grayston et al. (1995) Journal of Infectious Diseases 168: 1231; Grayston et al (1990) Journal of Infectious Diseases 161:618; Marrie (1993) Clinical Infectious Diseases. 18:501; Wang et al (1986) Chlamydial infections Cambridge University Press, Cambridge. p. 329. The great majority of the adult population (over 60%) has antibodies to *C. pneumoniae* (Wang et al (1986) Chlamydial infections. Cambridge University Press, Cambridge. p. 329), indicating past infection which was unrecognized or asymptomatic.

*C. pneumoniae* infection usually presents as an acute respiratory disease (i.e., cough, sore throat, hoarseness, and fever; abnormal chest sounds on auscultation). For most patients, the cough persists for 2 to 6 weeks, and recovery is slow. In approximately 10% of these cases, upper respiratory tract infection is followed by bronchitis or pneumonia. Furthermore, during a *C. pneumoniae* epidemic, subsequent co-infection with pneumococcus has been noted in about half of these pneumonia patients, particularly in the infirm and the elderly. As noted above, there is more and more evidence that *C. pneumoniae* infection is also linked to diseases other than respiratory infections.

The reservoir for the organism is presumably people. In contrast to *C. psittaci* infections, there is no known bird or animal reservoir. Transmission has not been clearly defined. It may result from direct contact with secretions, from fomites, or from airborne spread. There is a long incubation period, which may last for many months. Based on analysis of epidemics, *C. pneumoniae* appears to spread slowly through a population (case-to-case interval averaging 30 days) because infected persons are inefficient transmitters of the organism. Susceptibility to *C. pneumoniae* is universal. Reinfections occur during adulthood, following the primary infection as a child. *C. pneumoniae* appears to be an endemic disease throughout the world, noteworthy for superimposed intervals of increased incidence (epidemics) that persist for 2 to 3 years. *C. trachomatis* infection does not confer cross-immunity to *C. pneumoniae*. Infections are easily treated with oral antibiotics, tetracycline or erythromycin (2 g/d, for at least 10 to 14 d). A recently developed drug, azithromycin, is highly effective as a single-dose therapy against chlamydial infections.

In most instances, *C. pneumoniae* infection is often mild and without complications, and up to 90% of infections are subacute or unrecognized. Among children in industrialized countries, infections have been thought to be rare up to the age of 5 y, although a recent study (E Normann et al, *Chlamydia pneumoniae* in children with acute respiratory tract infections, Acta Paediatrica, 1998, Vol 87, Iss 1, pp 23–27) has reported that many children in this age group show PCR evidence of infection despite being seronegative, and estimates a prevalence of 17–19% in 2–4 y olds. In developing countries, the seroprevalence of *C. pneumoniae* antibodies among young children is elevated, and there are suspicions that *C. pneumoniae* may be an important cause of acute lower respiratory tract disease and mortality for infants and children in tropical regions of the world.

From seroprevalence studies and studies of local epidemics, the initial *C. pneumoniae* infection usually happens between the ages of 5 and 20 y. In the USA, for example, there are estimated to be 30,000 cases of childhood pneumonia each year caused by *C. pneumoniae*. Infections may cluster among groups of children or young adults (e.g., school pupils or military conscripts).

*C. pneumoniae* causes 10 to 25% of community-acquired lower respiratory tract infections (as reported from Sweden, Italy, Finland, and the USA). During an epidemic, *C. pneumonia* infection may account for 50 to 60% of the cases of pneumonia. During these periods, also, more episodes of mixed infections with *S. pneumoniae* have been reported.

Reinfection during adulthood is common; the clinical presentation tends to be milder. Based on population seroprevalence studies, there tends to be increased exposure with age, which is particularly evident among men. Some investigators have speculated that a persistent, asymptomatic *C. pneumoniae* infection state is common.

In adults of middle age or older, *C. pneumoniae* infection may progress to chronic bronchitis and sinusitis. A study in the USA revealed that the incidence of pneumonia caused by *C. pneumoniae* in persons younger than 60 years is 1 case per 1,000 persons per year; but in the elderly, the disease incidence rose three-fold. *C. pneumoniae* infection rarely leads to hospitalization, except in patients with an underlying illness.

Of considerable importance is the association of atherosclerosis and *C. pneumoniae* infection. There are several epidemiological studies showing a correlation of previous infections with *C. pneumoniae* and heart attacks, coronary artery and carotid artery disease (Saikku et al. (1988) Lancet;ii:983; Thom et al. (1992) JAMA 268:68; Linnanmaki et al. (1993), Circulation 87:1030; Saikku et al. (1992) Annals Internal Medicine 116:273; Melnick et al(1993) American Journal of Medicine 95:499). Moreover, the organisms has been detected in atheromas and fatty streaks of the coronary, carotid, peripheral arteries and aorta (Shor et al. (1992) South African. Medical Journal 82:158; Kuo et al. (1993) Journal of Infectious Diseases 167:841; Kuo et al. (1993) Arteriosclerosis and Thrombosis 13:1500; Campbell et al (1995) Journal of Infectious Diseases 172:585; Chiu et al. Circulation, 1997 (In Press)). Viable *C. pneumoniae* has been recovered from the coronary and carotid artery (Ramirez et al (1996) Annals of Internal Medicine 125:979; Jackson et al. Abst. K121, p272, 36$^{th}$ ICAAC, 15–18 Sep. 1996, New Orleans). Furthermore, it has been shown that *C. pneumoniae* can induce changes of atherosclerosis in a rabbit model (Fong et al (1997) Journal of Clinical Microbiolology 35:48). Taken together, these results indicate that it is highly probable that *C. pneumoniae* can cause atherosclerosis in humans, though the epidemiological importance of chlamydial atherosclerosis remains to be demonstrated.

A number of recent studies have also indicated an association between *C. pneumoniae* infection and asthma. Infection has been linked to wheezing, asthmatic bronchitis, adult-onset asthma and acute exacerbations of asthma in adults, and small-scale studies have shown that prolonged antibiotic treatment was effective at greatly reducing the severity of the disease in some individuals (Hahn D L, et al. Evidence for *Chlamydia pneumoniae* infection in steroid-dependent asthma.Ann Allergy Asthma Immunol. 1998 January; 80(1): 45–49.; Hahn D L, et al. Association of *Chlamydia pneumoniae* IgA antibodies with recently symptomatic asthma. Epidemiol Infect. 1996 December; 117(3): 513–517; Bjornsson E, et al. Serology of chlamydia in relation to asthma and bronchial hyperresponsiveness. Scand J Infect Dis. 1996; 28(1): 63–69.; Hahn D L. Treatment of *Chlamydia pneumoniae* infection in adult asthma: a before-after trial. J Fam Pract. 1995 October; 41(4): 345–351.; Allegra L, et al. Acute exacerbations of asthma in adults: role of *Chlamydia pneumoniae* infection. Eur Respir J. 1994 December; 7(12): 2165–2168.; Hahn D L, et al. Association of *Chlamydia pneumoniae* (strain TWAR) infection with wheezing, asthmatic bronchitis, and adult-onset asthma. JAMA. 1991 Jul. 10; 266(2): 225–230).

In light of these results a protective vaccine against *C. pneumoniae* infection would be of considerable importance. There is not yet an effective vaccine for any human chlamydial infection. It is conceivable that an effective vaccine can be developed using physically or chemically inactivated Chlamydiae. However, such a vaccine does not have a high margin of safety. In general, safer vaccines are made by genetically manipulating the organism by attenuation or by recombinant means. Accordingly, a major obstacle in creating an effective and safe vaccine against human chlamydial infection has been the paucity of genetic information regarding *Chlamydia*, specifically *C. pneumoniae*.

Studies with *C. trachomatis* and *C. psittaci* indicate that safe and effective vaccine against *Chlamydia* is an attainable goal. For example, mice which have recovered from a lung infection with *C. trachomatis* are protected from infertility induced by a subsequent vaginal challenge (Pal et al. (1996) Infection and Immunity. 64:5341). Similarly, sheep immunized with inactivated *C. psittaci* were protected from subsequent chlamydial-induced abortions and stillbirths (Jones et al. (1995) Vaccine 13:715). Protection from chlamydial infections has been associated with Th1 immune responses, particularly the induction of INFg—producing CD4+T-cells (Igietsemes et al. (1993) Immunology 5:317). The adoptive transfer of CD4+ cell lines or clones to nude or SCID mice conferred protection from challenge or cleared chronic disease (Igietseme et al (1993) Regional Immunology 5:317; Magee et al (1993) Regional Immunology 5: 305), and in vivo depletion of CD4+ T cells exacerbated disease post-challenge (Landers et al (1991) Infection & Immunity 59:3774; Magee et al (1995) Infection & Immunity 63:516). However, the presence of sufficiently high titres of neutralising antibody at mucosal surfaces can also exert a protective effect (Cotter et al. (1995) Infection and Immunity 63:4704).

Antigenic variation within the species *C. pneumoniae* is not well documented due to insufficient genetic information, though variation is expected to exist based on *C. trachomatis*. Serovars of *C. trachomatis* are defined on the basis of antigenic variation in the major outer membrane protein (MOMP), but published *C. pneumoniae* MOMP gene sequences show no variation between several diverse isolates of the organism (Campbell et al (1990) Infection and Immunity 58:93; McCafferty et al (1995) Infection and Immunity 63:2387–9; Knudsen et al (1996) Third Meeting of the European Society for Chlamydia Research, Vienna). The gene encoding a 76 kDa antigen has been cloned from a single strain of *C. pneumoniae* and the sequence published (Perez Melgosa et al., Infect. Immun. 1994. 62:880). An operon encoding the 9 kDa and 60 kDa cyteine-rich outer membrane protein genes has been described (Watson et al., Nucleic Acids Res (1990) 18:5299; Watson et al., Microbiology (1995) 141:2489). Many antigens recognized by immune sera to *C. pneumoniae* are conserved across all chlamydiae, but 98 kDa, 76 kDa and several other proteins may be *C. pneumoniae*-specific (Perez Melgosa et al., Infect. Immun. 1994. 62:880; Melgosa et al., FEMS Microbiol Lett (1993) 112:199;, Campbell et al., J Clin Microbiol (1990) 28:1261; Iijima et al., J Clin Microbiol (1994) 32:583). An assessment of the number and relative frequency of any *C. pneumoniae* serotypes, and the defining antigens, is not yet possible. The entire genome sequence of *C. pneumoniae* strain CWL-029 is now known (http://chlamydia-www.berkeley.edu:4231/) and as further sequences become available a better understanding of antigenic variation may be gained.

Many antigens recognised by immune sera to *C. pneumoniae* are conserved across all chlamydiae, but 98 kDa, 76 kDa and 54 kDa proteins appear to be *C. pneumoniae*-specific (Campos et al. (1995) Investigation of Ophthalmology and Visual Science 36:1477; Marrie (1993) Clinical Infectious Diseases. 18:501; Wiedmann-Al-Ahmad M, et al. Reactions of polyclonal and neutralizing anti-p54 monoclonal antibodies with an isolated, species-specific 54-kilodalton protein of *Chlamydia pneumoniae*. Clin Diagn Lab Immunol. 1997 November; 4(6): 700–704).

Immunoblotting of isolates with sera from patients does show variation of blotting patterns between isolates, indicating that serotypes *C. pneumoniae* may exist (Grayston et al. (1995) Journal of Infectious Diseases 168:1231; Ramirez et al (1996) Annals of Internal Medicine 125:979). However, the results are potentially confounded by the infection status of the patients, since immunoblot profiles of a patient's sera change with time post-infection. An assessment of the number and relative frequency of any serotypes, and the defining antigens, is not yet possible.

Accordingly, a need exists for identifying and isolating polynucleotide sequences of *C. pneumoniae* for use in preventing and treating *Chlamydia* infection.

SUMMARY OF THE INVENTION

The present invention provides purified and isolated polynucleotide molecules that encode the *Chlamydia* polypeptides designated 60 kDa cysteine-rich membrane proteine (SEQ ID No: 1) which can be used in methods to prevent, treat, and diagnose *Chlamydia* infection. In one form of the invention, the polynucleotide molecules are DNA that encode the polypeptide of SEQ ID No: 2.

Another form of the invention provides polypeptides corresponding to the isolated DNA molecules. The amino acid sequence of the corresponding encoded polypeptide is shown as SEQ ID No: 2.

Those skilled in the art will readily understand that the invention, having provided the polynucleotide sequences encoding the *Chlamydia* 60 kDa cysteine-rich membrane protein, also provides polynucleotides encoding fragments derived from such a polypeptide. Moreover, the invention is understood to provide mutants and derivatives of such polypeptides and fragments derived therefrom, which result from the addition, deletion, or substitution of non-essential amino acids as described herein. Those skilled in the art would also readily understand that the invention, having provided the polynucleotide sequences encoding *Chlamydia* polypeptides, further provides monospecific antibodies that specifically bind to such polypeptides.

The present invention has wide application and includes expression cassettes, vectors, and cells transformed or transfected with the polynucleotides of the invention. Accordingly, the present invention further provides (i) a method for producing a polypeptide of the invention in a recombinant host system and related expression cassettes, vectors, and transformed or transfected cells; (ii) a vaccine, or a live vaccine vector such as a pox virus, *Salmonella typhimurium*, or *Vibrio cholerae* vector, containing a polynucleotide of the invention, such vaccines and vaccine vectors being useful for, e.g., preventing and treating *Chlamydia* infection, in combination with a diluent or carrier, and related pharmaceutical compositions and associated therapeutic and/or prophylactic methods; (iii) a therapeutic and/or prophylactic use of an RNA or DNA molecule of the invention, either in a naked form or formulated with a delivery vehicle, a polypeptide or combination of polypeptides, or a monospecific antibody of the invention, and related pharmaceutical compositions; (iv) a method for diagnosing the presence of *Chlamydia* in a biological sample, which can involve the use of a DNA or RNA molecule, a monospecific antibody, or a polypeptide of the invention; and (v) a method for purifying a polypeptide of the invention by antibody-based affinity chromatography.

BRIEF DESCRIPTION OF THE DRAWINGS

The present invention will be further understood from the following description with reference to the drawings, in which:

Figure 2:
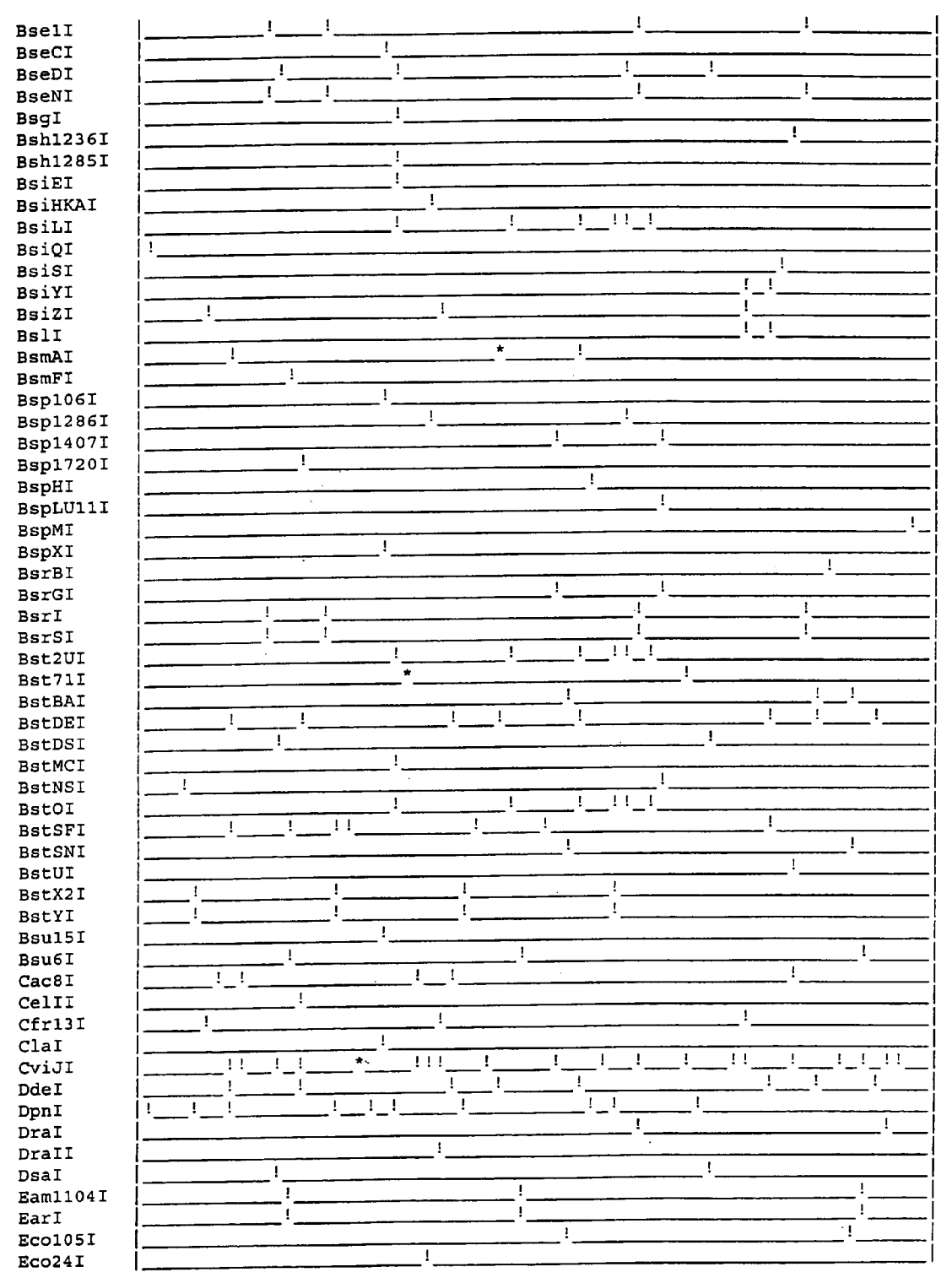
Figure 2:
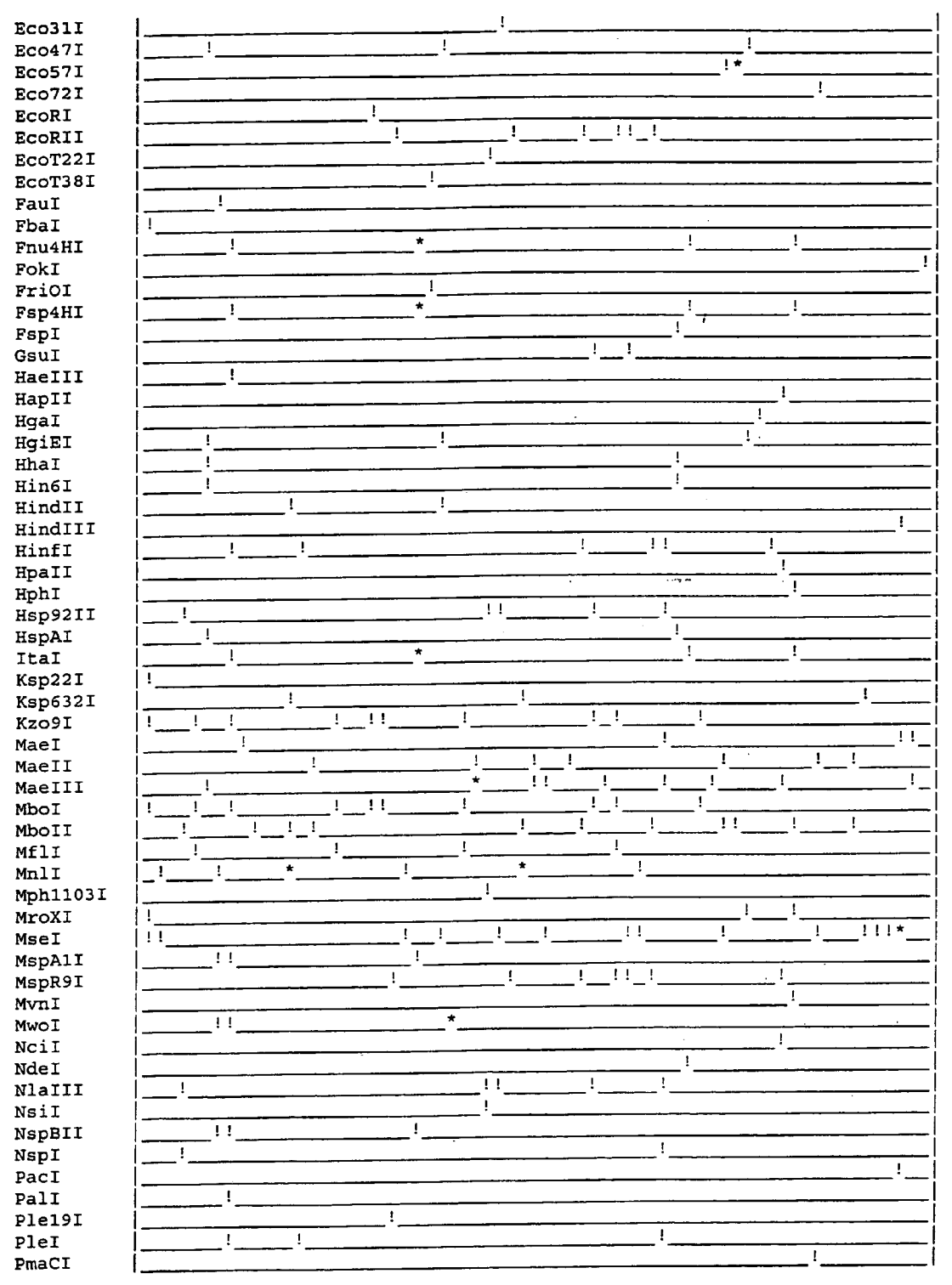

FIG. 2 shows the restriction enzyme analysis of the *C. pneumoniae* 60 kDa cysteine-rich membrane protein gene.

FIG. 4 illustrates protection against *C. pneumoniae* infection by pCACRMP60 following DNA immunization.

DETAILED DESCRIPTION OF INVENTION

Figure 1:
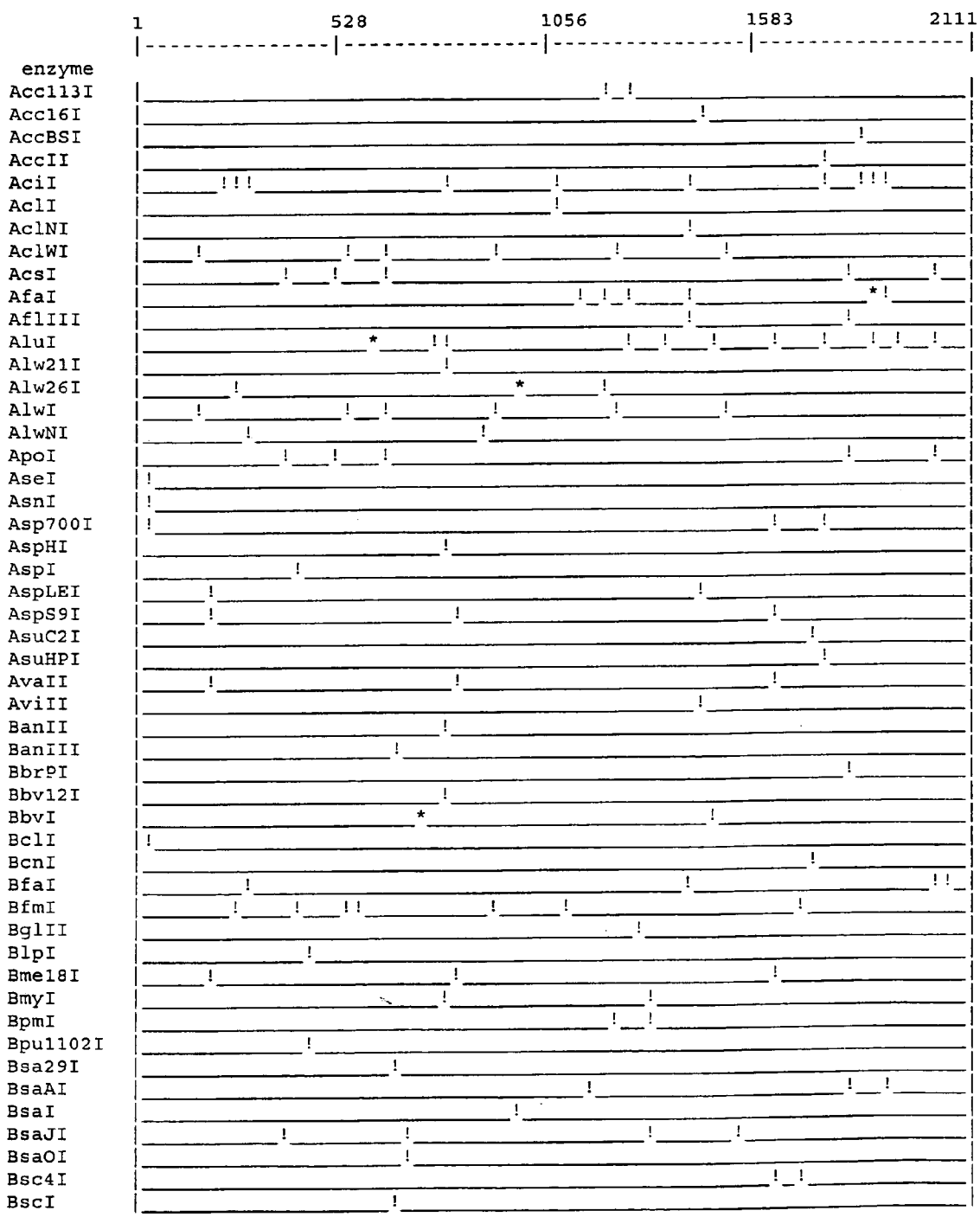
FIG. 1 shows the nucleotide sequence of the 60 kDa cysteine-rich membrane protein gene (SEQ ID No: 1) and the deduced amino acid sequence of the 60 kDa cysteine-rich membrane protein from *Chlamydia pneumoniae* (SEQ ID No: 2).
Figure 3:
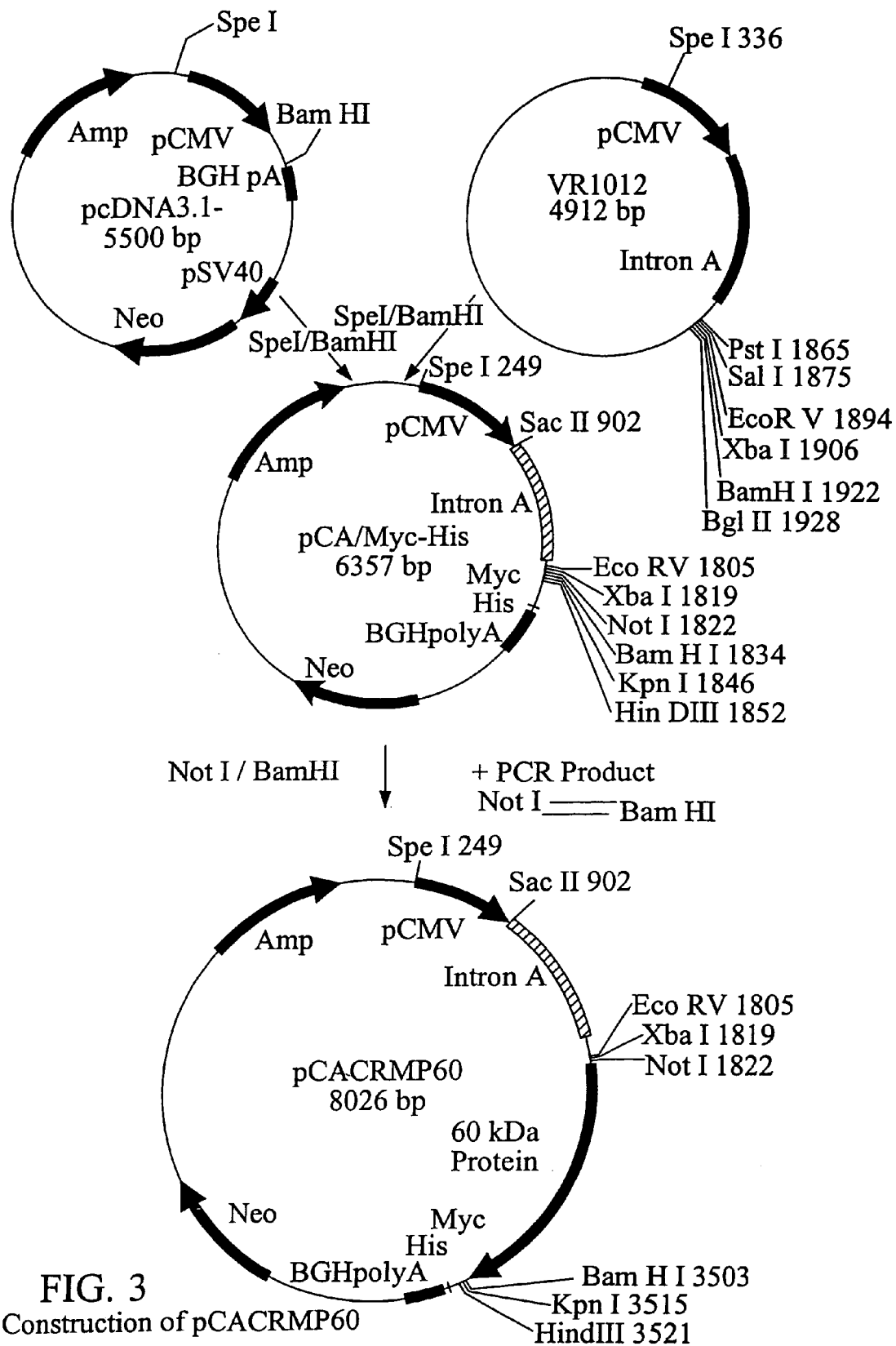
FIG. 3 shows the construction and elements of plasmid pCACRMP60.

An open reading frame (ORF) encoding the chlamydial 60 kDa cysteine-rich membrane protein has been identified from the *C. pneumoniae* genome. The gene encoding this protein has been inserted into an expression plasmid and shown to confer immune protection against chlamydial infection. Accordingly, this 60 kDa cysteine-rich membrane protein and related polypeptides can be used to prevent and treat *Chlamydia* infection.

According to a first aspect of the invention, isolated polynucleotides are provided which encode *Chlamydia* polypeptides, whose amino acid sequences are shown in SEQ ID No: 2.

The term "isolated polynucleotide" is defined as a polynucleotide removed from the environment in which it naturally occurs. For example, a naturally-occurring DNA molecule present in the genome of a living bacteria or as part of a gene bank is not isolated, but the same molecule separated from the remaining part of the bacterial genome, as a result of, e.g., a cloning event (amplification), is isolated. Typically, an isolated DNA molecule is free from DNA regions (e.g., coding regions) with which it is immediately contiguous at the 5' or 3' end, in the naturally occurring genome. Such isolated polynucleotides may be part of a vector or a composition and still be defined as isolated in that such a vector or composition is not part of the natural environment of such polynucleotide.

The polynucleotide of the invention is either RNA or DNA (cDNA, genomic DNA, or synthetic DNA), or modifications, variants, homologs or fragments thereof. The DNA is either double-stranded or single-stranded, and, if single-stranded, is either the coding strand or the non-coding (anti-sense) strand. Any one of the sequences that encode the polypeptides of the invention as shown in SEQ ID No: 1 is (a) a coding sequence, (b) a ribonucleotide sequence derived from transcription of (a), or (c) a coding sequence which uses the redundancy or degeneracy of the genetic code to encode the same polypeptides. By "polypeptide" or "protein" is meant any chain of amino acids, regardless of length or post-translational modification (e.g., glycosylation or phosphorylation). Both terms are used interchangeably in the present application.

Consistent with the first aspect of the invention, amino acid sequences are provided which are homologous to SEQ ID No: 2. As used herein, "homologous amino acid sequence" is any polypeptide which is encoded, in whole or in part, by a nucleic acid sequence which hybridizes at 25–35° C. below critical melting temperature (Tm), to any portion of the nucleic acid sequence of SEQ ID No: 1. A homologous amino acid sequence is one that differs from an amino acid sequence shown in SEQ ID No: 2 by one or more conservative amino acid substitutions. Such a sequence also encompass serotypic variants (defined below) as well as sequences containing deletions or insertions which retain inherent characteristics of the polypeptide such as immunogenicity. Preferably, such a sequence is at least 75%, more preferably 80%, and most preferably 90% identical to SEQ ID No: 2.

Homologous amino acid sequences include sequences that are identical or substantially identical to SEQ ID No: 2. By "amino acid sequence substantially identical" is meant a sequence that is at least 90%, preferably 95%, more preferably 97%, and most preferably 99% identical to an amino acid sequence of reference and that preferably differs from the sequence of reference by a majority of conservative amino acid substitutions.

Conservative amino acid substitutions are substitutions among amino acids of the same class. These classes include, for example, amino acids having uncharged polar side chains, such as asparagine, glutamine, serine, threonine, and tyrosine; amino acids having basic side chains, such as lysine, arginine, and histidine; amino acids having acidic side chains, such as aspartic acid and glutamic acid; and amino acids having nonpolar side chains, such as glycine, alanine, valine, leucine, isoleucine, proline, phenylalanine, methionine, tryptophan, and cysteine.

Homology is measured using sequence analysis software such as Sequence Analysis Software Package of the Genetics Computer Group, University of Wisconsin Biotechnology Center, 1710 University Avenue, Madison, Wis. 53705. Amino acid sequences are aligned to maximize identity. Gaps may be artificially introduced into the sequence to attain proper alignment. Once the optimal alignment has been set up, the degree of homology is established by recording all of the positions in which the amino acids of both sequences are identical, relative to the total number of positions.

Homologous polynucleotide sequences are defined in a similar way. Preferably, a homologous sequence is one that is at least 45%, more preferably 60%, and most preferably 85% identical to the coding sequence of SEQ ID No: 1.

Consistent with the first aspect of the invention, polypeptides having a sequence homologous to SEQ ID No: 2 include naturally-occurring allelic variants, as well as mutants or any other non-naturally occurring variants that retain the inherent characteristics of the polypeptide of SEQ ID No: 2.

As is known in the art, an allelic variant is an alternate form of a polypeptide that is characterized as having a substitution, deletion, or addition of one or more amino acids that does not alter the biological function of the polypeptide. By "biological function" is meant the function of the polypeptide in the cells in which it naturally occurs, even if the function is not necessary for the growth or survival of the cells. For example, the biological function of a porin is to allow the entry into cells of compounds present in the extracellular medium. Biological function is distinct from antigenic property. A polypeptide can have more than one biological function.

Allelic variants are very common in nature. For example, a bacterial species such as C. pneumoniae, is usually represented by a variety of strains that differ from each other by minor allelic variations. Indeed, a polypeptide that fulfills the same biological function in different strains can have an amino acid sequence (and polynucleotide sequence) that is not identical in each of the strains. Despite this variation, an immune response directed generally against many allelic variants has been demonstrated. In studies of the *Chlamydial* MOMP antigen, cross-strain antibody binding plus neutralization of infectivity occurs despite amino acid sequence variation of MOMP from strain to strain, indicating that the MOMP, when used as an immunogen, is tolerant of amino acid variations.

Polynucleotides encoding homologous polypeptides or allelic variants are retrieved by polymerase chain reaction (PCR) amplification of genomic bacterial DNA extracted by conventional methods. This involves the use of synthetic oligonucleotide primers matching upstream and downstream of the 5' and 3' ends of the encoding domain. Suitable primers are designed according to the nucleotide sequence information provided in SEQ ID No:1. The procedure is as follows: a primer is selected which consists of 10 to 40, preferably 15 to 25 nucleotides. It is advantageous to select primers containing C and G nucleotides in a proportion sufficient to ensure efficient hybridization; i.e., an amount of C and G nucleotides of at least 40%, preferably 50% of the total nucleotide content. A standard PCR reaction contains typically 0.5 to 5 Units of Taq DNA polymerase per 100 μL, 20 to 200 μM deoxynucleotide each, preferably at equivalent concentrations, 0.5 to 2.5 mM magnesium over the total deoxynucleotide concentration, $10^5$ to $10^6$ target molecules, and about 20 pmol of each primer. About 25 to 50 PCR cycles are performed, with an annealing temperature 15° C. to 5° C. below the true Tm of the primers. A more stringent annealing temperature improves discrimination against incorrectly annealed primers and reduces incorporation of incorrect nucleotides at the 3' end of primers. A denaturation temperature of 95° C. to 97° C. is typical, although higher temperatures may be appropriate for dematuration of G+C-rich targets. The number of cycles performed depends on the starting concentration of target molecules, though typically more than 40 cycles is not recommended as non-specific background products tend to accumulate.

An alternative method for retrieving polynucleotides encoding homologous polypeptides or allelic variants is by hybridization screening of a DNA or RNA library. Hybridization procedures are well-known in the art and are described in Ausubel et al., (Ausubel et al., Current Protocols in Molecular Biology, John Wiley & Sons Inc., 1994), Silhavy et al. (Silhavy et al. Experiments with Gene Fusions, Cold Spring Harbor Laboratory Press, 1984), and Davis et al. (Davis et al. A Manual for Genetic Engineering: Advanced Bacterial Genetics, Cold Spring Harbor Laboratory Press, 1980)). Important parameters for optimizing hybridization conditions are reflected in a formula used to obtain the critical melting temperature above which two complementary DNA strands separate from each other (Casey & Davidson, Nucl. Acid Res. (1977) 4:1539). For polynucleotides of about 600 nucleotides or larger, this formula is as follows: $Tm=81.5+0.41\times(\% \ G+C)+16.6 \log$ (cation ion concentration)$-0.63\times(\%$ formamide$)-600$/base number. Under appropriate stringency conditions, hybridization temperature (Th) is approximately 20 to 40° C., 20 to 25° C., or, preferably 30 to 40° C. below the calculated Tm. Those skilled in the art will understand that optimal temperature and salt conditions can be readily determined.

For the polynucleotides of the invention, stringent conditions are achieved for both pre-hybridizing and hybridizing incubations (i) within 4–16 hours at 42° C., in 6×SSC containing 50% formamide, or (ii) within 4–16 hours at 65° C. in an aqueous 6×SSC solution (1 M NaCl, 0.1 M sodium citrate (pH 7.0)). Typically, hybridization experiments are performed at a temperature from 60 to 68° C., e.g. 65° C. At such a temperature, stringent hybridization conditions can be achieved in 6×SSC, preferably in 2×SSC or 1×SSC, more preferably in 0.5×SSc, 0.3×SSC or 0.1×SSC (in the absence of formamide). 1×SSC contains 0.15 M NaCl and 0.015 M sodium citrate.

Useful homologs and fragments thereof that do not occur naturally are designed using known methods for identifying regions of an antigen that are likely to tolerate amino acid sequence changes and/or deletions. As an example, homologous polypeptides from different species are compared; conserved sequences are identified. The more divergent sequences are the most likely to tolerate sequence changes. Homology among sequences may be analyzed using, as an example, the BLAST homology searching algorithm of Altschul et al., Nucleic Acids Res.; 25:3389–3402 (1997). Alternatively, sequences are modified such that they become more reactive to T- and/or B-cells, based on computer-assisted analysis of probable T- or B-cell epitopes Yet another alternative is to mutate a particular amino acid residue or sequence within the polypeptide in vitro, then screen the mutant polypeptides for their ability to prevent or treat *Chlamydia* infection according to the method outlined below.

A person skilled in the art will readily understand that by following the screening process of this invention, it will be determined without undue experimentation whether a particular homolog of SEQ ID No. 2 may be useful in the prevention or treatment of *Chlamydia* infection. The screening procedure comprises the steps:

(i) immunizing an animal, preferably mouse, with the test homolog or fragment;

(ii) inoculating the immunized animal with *Chlamydia*; and (iii) selecting those homologs or fragments which confer protection against *Chlamydia*.

By "conferring protection" is meant that there is a reduction in severity of any of the effects of *Chlamydia* infection, in comparison with a control animal which was not immunized with the test homolog or fragment.

Consistent with the first aspect of the invention, polypeptide derivatives are provided that are partial sequences of SEQ ID No. 2, partial sequences of polypeptide sequences homologous to SEQ ID No. 2, polypeptides derived from full-length polypeptides by internal deletion, and fusion proteins.

It is an accepted practice in the field of immunology to use fragments and variants of protein immunogens as vaccines, as all that is required to induce an immune response to a protein is a small (e.g., 8 to 10 amino acid) immunogenic region of the protein. Various short synthetic peptides corresponding to surface-exposed antigens of pathogens other than *Chlamydia* have been shown to be effective vaccine antigens against their respective pathogens, e.g. an 11 residue peptide of murine mammary tumor virus (Casey & Davidson, Nucl. Acid Res. (1977) 4:1539), a 16-residue peptide of Semliki Forest virus (Snijders et al., 1991. J. Gen. Virol. 72:557–565), and two overlapping peptides of 15 residues each from canine parvovirus (Langeveld et al., Vaccine 12(15):1473–1480, 1994).

Accordingly, it will be readily apparent to one skilled in the art, having read the present description, that partial sequences of SEQ ID No: 2 or their homologous amino acid sequences are inherent to the full-length sequences and are taught by the present invention. Such polypeptide fragments preferably are at least 12 amino acids in length. Advantageously, they are at least 20 amino acids, preferably at least 50 amino acids, more preferably at least 75 amino acids, and most preferably at least 100 amino acids in length.

Polynucleotides of 30 to 600 nucleotides encoding partial sequences of sequences homologous to SEQ ID No: 2 are retrieved by PCR amplification using the parameters outlined above and using primers matching the sequences upstream and downstream of the 5' and 3' ends of the fragment to be amplified. The template polynucleotide for such amplification is either the full length polynucleotide homologous to SEQ ID No: 1, or a polynucleotide contained in a mixture of polynucleotides such as a DNA or RNA library. As an alternative method for retrieving the partial sequences, screening hybridization is carried out under conditions described above and using the formula for calculating Tm. Where fragments of 30 to 600 nucleotides are to be retrieved, the calculated Tm is corrected by subtracting (600/polynucleotide size in base pairs) and the stringency conditions are defined by a hybridization temperature that is 5 to 10° C. below Tm. Where oligonucleotides shorter than 20–30 bases are to be obtained, the formula for calculating the Tm is as follows: Tm=4×(G+C)+2 (A+T). For example, an 18 nucleotide fragment of 50% G+C would have an approximate Tm of 54° C. Short peptides that are fragments of SEQ ID No: 2 or its homologous sequences, are obtained directly by chemical synthesis (E. Gross and H. J. Meinhofer, 4 The Peptides: Analysis, Synthesis, Biology; Modern Techniques of Peptide Synthesis, John Wiley & Sons (1981), and M. Bodanzki, Principles of Peptide Synthesis, Springer-Verlag (1984)).

Useful polypeptide derivatives, e.g., polypeptide fragments, are designed using computer-assisted analysis of amino acid sequences. This would identify probable surface-exposed, antigenic regions (Hughes et al., 1992. Infect. Immun. 60(9):3497). Analysis of 6 amino acid sequences contained in SEQ ID No: 2, based on the product of flexibility and hydrophobicity propensities using the program SEQSEE (Wishart D S, et al. "SEQSEE: a comprehensive program suite for protein sequence analysis." *Comput Appl Biosci.* 1994 April;10(2):121–32), can reveal potential B- and T-cell epitopes which may be used as a basis for selecting useful immunogenic fragments and variants. This analysis uses a reasonable combination of external surface features that is likely to be recognized by antibodies. Probable T-cell epitopes for HLA-A0201 MHC subclass may be revealed by an algorithms that emulate an approach developed at the NIH (Parker K C, et al. "Peptide binding to MHC class I molecules: implications for antigenic peptide prediction." *Immunol Res* 1995;14(1):34–57).

Epitopes which induce a protective T cell-dependent immune response are present throughout the length of the polypeptide. However, some epitopes may be masked by secondary and tertiary structures of the polypeptide. To reveal such masked epitopes large internal deletions are created which remove much of the original protein structure and exposes the masked epitopes. Such internal deletions sometimes effect the additional advantage of removing immunodominant regions of high variability among strains.

Polynucleotides encoding polypeptide fragments and polypeptides having large internal deletions are constructed using standard methods (Ausubel et al., Current Protocols in Molecular Biology, John Wiley & Sons Inc., 1994). Such methods include standard PCR, inverse PCR, restriction enzyme treatment of cloned DNA molecules, or the method of Kunkel et al. (Kunkel et al. Proc. Natl. Acad. Sci. USA (1985) 82:448). Components for these methods and instructions for their use are readily available from various commercial sources such as Stratagene. Once the deletion mutants have been constructed, they are tested for their ability to prevent or treat *Chlamydia* infection as described above.

As used herein, a fusion polypeptide is one that contains a polypeptide or a polypeptide derivative of the invention fused at the N- or C-terminal end to any other polypeptide (hereinafter referred to as a peptide tail). A simple way to obtain such a fusion polypeptide is by translation of an in-frame fusion of the polynucleotide sequences, i.e., a hybrid gene. The hybrid gene encoding the fusion polypeptide is inserted into an expression vector which is used to transform or transfect a host cell. Alternatively, the polynucleotide sequence encoding the polypeptide or polypeptide derivative is inserted into an expression vector in which the polynucleotide encoding the peptide tail is already present. Such vectors and instructions for their use are commercially available, e.g. the pMal-c2 or pMal-p2 system from New England Biolabs, in which the peptide tail is a maltose binding protein, the glutathione-S-transferase system of Pharmacia, or the His-Tag system available from Novagen. These and other expression systems provide convenient means for further purification of polypeptides and derivatives of the invention.

An advantageous example of a fusion polypeptide is one where the polypeptide or homolog or fragment of the invention is fused to a polypeptide having adjuvant activity, such as subunit B of either cholera toxin or *E. coli* heat-labile toxin. Another advantageous fusion is one where the polypeptide, homolog or fragment is fused to a strong T-cell epitope or B-cell epitope. Such an epitope may be one known in the art (e.g. the Hepatitis B virus core antigen, D. R. Millich et al., "Antibody production to the nucleocapsid and envelope of the Hepatitis B virus primed by a single synthetic T cell site", Nature. 1987. 329:547–549), or one which has been identified in another polypeptide of the invention based on computer-assisted analysis of probable T- or B-cell epitopes. Consistent with this aspect of the invention is a fusion polypeptide comprising T- or B-cell epitopes from SEQ ID No: 2 or its homolog or fragment, wherein the epitopes are derived from multiple variants of said polypeptide or homolog or fragment, each variant differing from another in the location and sequence of its epitope within the polypeptide. Such a fusion is effective in the prevention and treatment of *Chlamydia* infection since it optimizes the T- and B-cell response to the overall polypeptide, homolog or fragment.

To effect fusion, the polypeptide of the invention is fused to the N-, or preferably, to the C-terminal end of the polypeptide having adjuvant activity or T- or B-cell epitope. Alternatively, a polypeptide fragment of the invention is inserted internally within the amino acid sequence of the polypeptide having adjuvant activity. The T- or B-cell epitope may also be inserted internally within the amino acid sequence of the polypeptide of the invention.

Consistent with the first aspect, the polynucleotides of the invention also encode hybrid precursor polypeptides containing heterologous signal peptides, which mature into polypeptides of the invention. By "heterologous signal peptide" is meant a signal peptide that is not found in naturally-occurring precursors of polypeptides of the invention.

Polynucleotide molecules according to the invention, including RNA, DNA, or modifications or combinations thereof, have various applications. A DNA molecule is used, for example, (i) in a process for producing the encoded polypeptide in a recombinant host system, (ii) in the construction of vaccine vectors such as poxviruses, which are further used in methods and compositions for preventing and/or treating *Chlamydia* infection, (iii) as a vaccine agent (as well as an RNA molecule), in a naked form or formulated with a delivery vehicle and, (iv) in the construction of attenuated *Chlamydia* strains that can over-express a polynucleotide of the invention or express it in a non-toxic, mutated form.

Accordingly, a second aspect of the invention encompasses (i) an expression cassette containing a DNA molecule of the invention placed under the control of the elements required for expression, in particular under the control of an appropriate promoter; (ii) an expression vector containing an expression cassette of the invention; (iii) a procaryotic or eucaryotic cell transformed or transfected with an expression cassette and/or vector of the invention, as well as (iv) a process for producing a polypeptide or polypeptide derivative encoded by a polynucleotide of the invention, which involves culturing a procaryotic or eucaryotic cell transformed or transfected with an expression cassette and/or vector of the invention, under conditions that allow expression of the DNA molecule of the invention and, recovering the encoded polypeptide or polypeptide derivative from the cell culture.

A recombinant expression system is selected from procaryotic and eucaryotic hosts. Eucaryotic hosts include yeast cells (e.g., *Saccharomyces cerevisiae* or *Pichia pastoris*), mammalian cells (e.g., COS1, NIH3T3, or JEG3 cells), arthropods cells (e.g., *Spodoptera frugiperda* (SF9) cells), and plant cells. A preferred expression system is a procaryotic host such as *E. coli*. Bacterial and eucaryotic cells are available from a number of different sources including commercial sources to those skilled in the art, e.g., the American Type Culture Collection (ATCC; Rockville, Md.). Commercial sources of cells used for recombinant protein expression also provide instructions for usage of the cells.

The choice of the expression system depends on the features desired for the expressed polypeptide. For example, it may be useful to produce a polypeptide of the invention in a particular lipidated form or any other form.

One skilled in the art would redily understand that not all vectors and expression control sequences and hosts would be expected to express equally well the polynucleotides of this invention. With the guidelines described below, however, a selection of vectors, expression control sequences and hosts may be made without undue experimentation and without departing from the scope of this invention.

In selecting a vector, the host must be chosen that is compatible with the vector which is to exist and possibly replicate in it. Considerations are made with respect to the vector copy number, the ability to control the copy number, expression of other proteins such as antibiotic resistance. In selecting an expression control sequence, a number of variables are considered. Among the important variable are the relative strength of the sequence (e.g. the ability to drive expression under various conditions), the ability to control the sequence's function, compatibility between the polynucleotide to be expressed and the control sequence (e.g. secondary structures are considered to avoid hairpin structures which prevent efficient transcription). In selecting the host, unicellular hosts are selected which are compatible with the selected vector, tolerant of any possible toxic effects of the expressed product, able to secrete the expressed product efficiently if such is desired, to be able to express the product in the desired conformation, to be easily scaled up, and to which ease of purification of the final product.

The choice of the expression cassette depends on the host system selected as well as the features desired for the expressed polypeptide. Typically, an expression cassette includes a promoter that is functional in the selected host system and can be constitutive or inducible; a ribosome binding site; a start codon (ATG) if necessary; a region encoding a signal peptide, e.g., a lipidation signal peptide; a DNA molecule of the invention; a stop codon; and optionally a 3' terminal region (translation and/or transcription terminator) The signal peptide encoding region is adjacent to the polynucleotide of the invention and placed in proper reading frame. The signal peptide-encoding region is homologous or heterologous to the DNA molecule encoding the mature polypeptide and is compatible with the secretion apparatus of the host used for expression. The open reading frame constituted by the DNA molecule of the invention, solely or together with the signal peptide, is placed under the control of the promoter so that transcription and translation occur in the host system. Promoters and signal peptide encoding regions are widely known and available to those skilled in the art and include, for example, the promoter of

*Salmonella typhimurium* (and derivatives) that is inducible by arabinose (promoter araB) and is functional in Gram-negative bacteria such as *E. coli* (as described in U.S. Pat. No. 5,028,530 and in Cagnon et al., (Cagnon et al., Protein Engineering (1991) 4(7):843)); the promoter of the gene of bacteriophage T7 encoding RNA polymerase, that is functional in a number of *E. coli* strains expressing T7 polymerase (described in U.S. Pat. No. 4,952,496); OspA lipidation signal peptide; and RlpB lipidation signal peptide (Takase et al., J. Bact. (1987) 169:5692).

The expression cassette is typically part of an expression vector, which is selected for its ability to replicate in the chosen expression system. Expression vectors (e.g., plasmids or viral vectors) can be chosen, for example, from those described in Pouwels et al. (Cloning Vectors: A Laboratory Manual 1985, Supp. 1987). Suitable expression vectors can be purchased from various commercial sources.

Methods for transforming/transfecting host cells with expression vectors are well-known in the art and depend on the host system selected as described in Ausubel et al., (Ausubel et al., Current Protocols in Molecular Biology, John Wiley & Sons Inc., 1994).

Upon expression, a recombinant polypeptide of the invention (or a polypeptide derivative) is produced and remains in the intracellular compartment, is secreted/excreted in the extracellular medium or in the periplasmic space, or is embedded in the cellular membrane. The polypeptide is recovered in a substantially purified form from the cell extract or from the supernatant after centrifugation of the recombinant cell culture. Typically, the recombinant polypeptide is purified by antibody-based affinity purification or by other well-known methods that can be readily adapted by a person skilled in the art, such as fusion of the polynucleotide encoding the polypeptide or its derivative to a small affinity binding domain. Antibodies useful for purifying by immunoaffinity the polypeptides of the invention are obtained as described below.

A polynucleotide of the invention can also be useful as a vaccine. There are two major routes, either using a viral or bacterial host as gene delivery vehicle (live vaccine vector) or administering the gene in a free form, e.g., inserted into a plasmid. Therapeutic or prophylactic efficacy of a polynucleotide of the invention is evaluated as described below.

Accordingly, a third aspect of the invention provides (i) a vaccine vector such as a poxvirus, containing a DNA molecule of the invention, placed under the control of elements required for expression; (ii) a composition of matter comprising a vaccine vector of the invention, together with a diluent or carrier; specifically (iii) a pharmaceutical composition containing a therapeutically or prophylactically effective amount of a vaccine vector of the invention; (iv) a method for inducing an immune response against *Chlamydia* in a mammal (e.g., a human; alternatively, the method can be used in veterinary applications for treating or preventing *Chlamydia* infection of animals, e.g., cats or birds), which involves administering to the mammal an immunogenically effective amount of a vaccine vector of the invention to elicit a protective or therapeutic immune response to *Chlamydia*; and particularly, (v) a method for preventing and/or treating a *Chlamydia* (e.g., *C. trachomatis, C. psittaci, C. pneumonia, C. pecorum*) infection, which involves administering a prophylactic or therapeutic amount of a vaccine vector of the invention to an infected individual. Additionally, the third aspect of the invention encompasses the use of a vaccine vector of the invention in the preparation of a medicament for preventing and/or treating *Chlamydia* infection.

As used herein, a vaccine vector expresses one or several polypeptides or derivatives of the invention. The vaccine vector may express additionally a cytokine, such as interleukin-2 (IL-2) or interleukin-12 (IL-12), that enhances the immune response (adjuvant effect). It is understood that each of the components to be expressed is placed under the control of elements required for expression in a mammalian cell.

Consistent with the third aspect of the invention is a composition comprising several vaccine vectors, each of them capable of expressing a polypeptide or derivative of the invention. A composition may also comprise a vaccine vector capable of expressing an additional *Chlamydia* antigen, or a subunit, fragment, homolog, mutant, or derivative thereof; optionally together with or a cytokine such as IL-2 or IL-12.

Vaccination methods for treating or preventing infection in a mammal comprises use of a vaccine vector of the invention to be administered by any conventional route, particularly to a mucosal (e.g., ocular, intranasal, oral, gastric, pulmonary, intestinal, rectal, vaginal, or urinary tract) surface or via the parenteral (e.g., subcutaneous, intradermal, intramuscular, intravenous, or intraperitoneal) route. Preferred routes depend upon the choice of the vaccine vector. Treatment may be effected in a single dose or repeated at intervals. The appropriate dosage depends on various parameters understood by skilled artisans such as the vaccine vector itself, the route of administration or the condition of the mammal to be vaccinated (weight, age and the like).

Live vaccine vectors available in the art include viral vectors such as adenoviruses and poxviruses as well as bacterial vectors, e.g., *Shigella, Salmonella, Vibrio cholerae, Lactobacillus*, Bacille bilié de Calmette-Guérin (BCG), and *Streptococcus*.

An example of an adenovirus vector, as well as a method for constructing an adenovirus vector capable of expressing a DNA molecule of the invention, are described in U.S. Pat. No. 4,920,209. Poxvirus vectors include vaccinia and canary pox virus, described in U.S. Pat. No. 4,722,848 and U.S. Pat. No. 5,364,773, respectively. (Also see, e.g., Tartaglia et al., Virology (1992) 188:217) for a description of a vaccinia virus vector and Taylor et al, Vaccine (1995) 13:539 for a reference of a canary pox.) Poxvirus vectors capable of expressing a polynucleotide of the invention are obtained by homologous recombination as described in Kieny et al., Nature (1984) 312:163 so that the polynucleotide of the invention is inserted in the viral genome under appropriate conditions for expression in mammalian cells. Generally, the dose of vaccine viral vector, for therapeutic or prophylactic use, can be of from about $1 \times 10^4$ to about $1 \times 10^{11}$, advantageously from about $1 \times 10^7$ to about $1 \times 10^{10}$, preferably of from about $1 \times 10^7$ to about $1 \times 10^9$ plaque-forming units per kilogram. Preferably, viral vectors are administered parenterally; for example, in 3 doses, 4 weeks apart. It is preferable to avoid adding a chemical adjuvant to a composition containing a viral vector of the invention and thereby minimizing the immune response to the viral vector itself.

Non-toxicogenic *Vibrio cholerae* mutant strains that are useful as a live oral vaccine are known. Mekalanos et al., Nature (1983) 306:551 and U.S. Pat. No. 4,882,278 describe strains which have a substantial amount of the coding sequence of each of the two ctxA alleles deleted so that no functional cholerae toxin is produced. WO 92/11354 describes a strain in which the irgA locus is inactivated by mutation; this mutation can be combined in a single strain with ctxA mutations. WO 94/01533 describes a deletion mutant lacking functional ctxA and attRS1 DNA sequences. These mutant strains are genetically engineered to express heterologous antigens, as described in WO 94/19482. An effective vaccine dose of a *Vibrio cholerae* strain capable of expressing a polypeptide or polypeptide derivative encoded by a DNA molecule of the invention contains about $1\times10^5$ to about $1\times10^9$, preferably about $1\times10^6$ to about $1\times10^8$, viable bacteria in a volume appropriate for the selected route of administration. Preferred routes of administration include all mucosal routes; most preferably, these vectors are administered intranasally or orally.

Attenuated *Salmonella typhimurium* strains, genetically engineered for recombinant expression of heterologous antigens or not, and their use as oral vaccines are described in Nakayama et al. (Bio/Technology (1988) 6:693) and WO 92/11361. Preferred routes of administration include all mucosal routes; most preferably, these vectors are administered intranasally or orally.

Other bacterial strains used as vaccine vectors in the context of the present invention are described for *Shigella flexneri* in High et al., EMBO (1992) 11:1991 and Sizemore et al., Science (1995) 270:299; for *Streptococcus gordonii* in Medaglini et al., Proc. Natl. Acad. Sci. USA (1995) 92:6868; and for Bacille Calmette Guerin in Flynn J. L., Cell. Mol. Biol. (1994) 40 (suppl. I):31, WO 88/06626, WO 90/00594, WO 91/13157, WO 92/01796, and WO 92/21376.

In bacterial vectors, the polynucleotide of the invention is inserted into the bacterial genome or remains in a free state as part of a plasmid.

The composition comprising a vaccine bacterial vector of the present invention may further contain an adjuvant. A number of adjuvants are known to those skilled in the art. Preferred adjuvants are selected as provided below.

Accordingly, a fourth aspect of the invention provides (i) a composition of matter comprising a polynucleotide of the invention, together with a diluent or carrier; (ii) a pharmaceutical composition comprising a therapeutically or prophylactically effective amount of a polynucleotide of the invention; (iii) a method for inducing an immune response against *Chlamydia* in a mammal by administration of an immunogenically effective amount of a polynucleotide of the invention to elicit a protective immune response to *Chlamydia*; and particularly, (iv) a method for preventing and/or treating a *Chlamydia* (e.g., *C. trachomatis, C. psittaci, C. pneumoniae*, or *C. pecorum*) infection, by administering a prophylactic or therapeutic amount of a polynucleotide of the invention to an infected individual. Additionally, the fourth aspect of the invention encompasses the use of a polynucleotide of the invention in the preparation of a medicament for preventing and/or treating *Chlamydia* infection. A preferred use includes the use of a DNA molecule placed under conditions for expression in a mammalian cell, especially in a plasmid that is unable to replicate in mammalian cells and to substantially integrate in a mammalian genome.

Use of the polynucleotides of the invention include their administration to a mammal as a vaccine, for therapeutic or prophylactic purposes. Such polynucleotides are used in the form of DNA as part of a plasmid that is unable to replicate in a mammalian cell and unable to integrate into the mammalian genome. Typically, such a DNA molecule is placed under the control of a promoter suitable for expression in a mammalian cell. The promoter functions either ubiquitously or tissue-specifically. Examples of non-tissue specific promoters include the early Cytomegalovirus (CMV) promoter (described in U.S. Pat. No. 5,168,062) and the Rous Sarcoma Virus promoter (described in Norton & Coffin, Molec. Cell Biol. (1985) 5:281). An example of a tissue-specific promoter is the desmin promoter which drives expression in muscle cells (Li et al., Gene (1989) 78:243, Li & Paulin, J. Biol. Chem. (1991) 266:6562 and Li & Paulin, J. Biol. Chem. (1993) 268:10403). Use of promoters is well-known to those skilled in the art. Useful vectors are described in numerous publications, specifically WO 94/21797 and Hartikka et al., Human Gene Therapy (1996) 7:1205.

Polynucleotides of the invention which are used as vaccines encode either a precursor or a mature form of the corresponding polypeptide. In the precursor form, the signal peptide is either homologous or heterologous. In the latter case, a eucaryotic leader sequence such as the leader sequence of the tissue-type plasminogen factor (tPA) is preferred.

As used herein, a composition of the invention contains one or several polynucleotides with optionally at least one additional polynucleotide encoding another *Chlamydia* antigen such as urease subunit A, B, or both, or a fragment, derivative, mutant, or analog thereof. The composition may also contain an additional polynucleotide encoding a cytokine, such as interleukin-2 (IL-2) or interleukin-12 (IL-12) so that the immune response is enhanced. These additional polynucleotides are placed under appropriate control for expression. Advantageously, DNA molecules of the invention and/or additional DNA molecules to be included in the same composition, are present in the same plasmid.

Standard techniques of molecular biology for preparing and purifying polynucleotides are used in the preparation of polynucleotide therapeutics of the invention. For use as a vaccine, a polynucleotide of the invention is formulated according to various methods outlined below.

One method utililizes the polynucleotide in a naked form, free of any delivery vehicles. Such a polynucleotide is simply diluted in a physiologically acceptable solution such as sterile saline or sterile buffered saline, with or without a carrier. When present, the carrier preferably is isotonic, hypotonic, or weakly hypertonic, and has a relatively low ionic strength, such as provided by a sucrose solution, e.g., a solution containing 20% sucrose.

An alternative method utilizes the polynucleotide in association with agents that assist in cellular uptake. Examples of such agents are (i) chemicals that modify cellular permeability, such as bupivacaine (see, e.g., WO 94/16737), (ii) liposomes for encapsulation of the polynucleotide, or (iii) cationic lipids or silica, gold, or tungsten microparticles which associate themselves with the polynucleotides.

Anionic and neutral liposomes are well-known in the art (see, e.g., Liposomes: A Practical Approach, RPC New Ed, IRL press (1990), for a detailed description of methods for making liposomes) and are useful for delivering a large range of products, including polynucleotides.

Cationic lipids are also known in the art and are commonly used for gene delivery. Such lipids include Lipofectin™ also known as DOTMA (N-[1-(2,3-dioleyloxy)propyl]-N,N,N-trimethylammonium chloride), DOTAP (1,2-bis (oleyloxy)-3-(trimethylammonio)propane), DDAB (dimethyldioctadecylammonium bromide), DOGS (dioctadecylamidologlycyl spermine) and cholesterol derivatives such as DC-Chol (3 beta-(N-(N',N'-dimethyl aminomethane)-carbamoyl) cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as described in WO 90/11092 as an example.

Formulation containing cationic liposomes may optionally contain other transfection-facilitating compounds. A number of them are described in WO 93/18759, WO 93/19768, WO 94/25608, and WO 95/02397. They include spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles are used for gene delivery, as described in WO 91/00359, WO 93/17706, and Tang et al. Nature (1992) 356:152. The microparticle-coated polynucleotide is injected via intradermal or intraepidermal routes using a needleless injection device ("gene gun"), such as those described in U.S. Pat. No. 4,945,050, U.S. Pat. No. 5,015,580, and WO 94/24263.

The amount of DNA to be used in a vaccine recipient depends, e.g., on the strength of the promoter used in the DNA construct, the immunogenicity of the expressed gene product, the condition of the mammal intended for administration (e.g., the weight, age, and general health of the mammal), the mode of administration, and the type of formulation. In general, a therapeutically or prophylactically effective dose from about 1 µg to about 1 mg, preferably, from about 10 µg to about 800 µg and, more preferably, from about 25 µg to about 250 µg, can be administered to human adults. The administration can be achieved in a single dose or repeated at intervals.

The route of administration is any conventional route used in the vaccine field. As general guidance, a polynucleotide of the invention is administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intraepidermal, or intramuscular route. The choice of administration route depends on the formulation that is selected. A polynucleotide formulated in association with bupivacaine is advantageously administered into muscles. When a neutral or anionic liposome or a cationic lipid, such as DOTMA or DC-Chol, is used, the formulation can be advantageously injected via intravenous, intranasal (aerosolization), intramuscular, intradermal, and subcutaneous routes. A polynucleotide in a naked form can advantageously be administered via the intramuscular, intradermal, or sub-cutaneous routes.

Although not absolutely required, such a composition can also contain an adjuvant. If so, a systemic adjuvant that does not require concomitant administration in order to exhibit an adjuvant effect is preferable such as, e.g., QS21, which is described in U.S. Pat. No. 5,057,546.

The sequence information provided in the present application enables the design of specific nucleotide probes and primers that are used for diagnostic purposes. Accordingly, a fifth aspect of the invention provides a nucleotide probe or primer having a sequence found in or derived by degeneracy of the genetic code from a sequence shown in SEQ ID No:1.

The term "probe" as used in the present application refers to DNA (preferably single stranded) or RNA molecules (or modifications or combinations thereof) that hybridize under the stringent conditions, as defined above, to nucleic acid molecules having SEQ ID No:1 or to sequences homologous to SEQ ID No:1, or to its complementary or anti-sense sequence. Generally, probes are significantly shorter than full-length sequences. Such probes contain from about 5 to about 100, preferably from about 10 to about 80, nucleotides. In particular, probes have sequences that are at least 75%, preferably at least 85%, more preferably 95% homologous to a portion of SEQ ID No:1 or that are complementary to such sequences. Probes may contain modified bases such as inosine, methyl-5-deoxycytidine, deoxyuridine, dimethylamino-5-deoxyuridine, or diamino-2,6-purine. Sugar or phosphate residues may also be modified or substituted. For example, a deoxyribose residue may be replaced by a polyamide (Nielsen et al., Science (1991) 254:1497) and phosphate residues may be replaced by ester groups such as diphosphate, alkyl, arylphosphonate and phosphorothioate esters. In addition, the 2'-hydroxyl group on ribonucleotides may be modified by including such groups as alkyl groups.

Probes of the invention are used in diagnostic tests, as capture or detection probes. Such capture probes are conventionally immobilized on a solid support, directly or indirectly, by covalent means or by passive adsorption. A detection probe is labelled by a detection marker selected from: radioactive isotopes, enzymes such as peroxidase, alkaline phosphatase, and enzymes able to hydrolyze a chromogenic, fluorogenic, or luminescent substrate, compounds that are chromogenic, fluorogenic, or luminescent, nucleotide base analogs, and biotin.

Probes of the invention are used in any conventional hybridization technique, such as dot blot (Maniatis et al., Molecular Cloning: A Laboratory Manual (1982) Cold Spring Harbor Laboratory Press, Cold Spring Harbor, N.Y.), Southern blot (Southern, J. Mol. Biol. (1975) 98:503), northern blot (identical to Southern blot with the exception that RNA is used as a target), or the sandwich technique (Dunn et al., Cell (1977) 12:23). The latter technique involves the use of a specific capture probe and/or a specific detection probe with nucleotide sequences that at least partially differ from each other.

A primer is a probe of usually about 10 to about 40 nucleotides that is used to initiate enzymatic polymerization of DNA in an amplification process (e.g., PCR), in an elongation process, or in a reverse transcription method. Primers used in diagnostic methods involving PCR are labeled by methods known in the art.

As described herein, the invention also encompasses (i) a reagent comprising a probe of the invention for detecting and/or identifying the presence of *Chlamydia* in a biological material; (ii) a method for detecting and/or identifying the presence of *Chlamydia* in a biological material, in which (a) a sample is recovered or derived from the biological material, (b) DNA or RNA is extracted from the material and denatured, and (c) exposed to a probe of the invention, for example, a capture, detection probe or both, under stringent hybridization conditions, such that hybridization is detected; and (iii) a method for detecting and/or identifying the presence of *Chlamydia* in a biological material, in which (a) a sample is recovered or derived from the biological material, (b) DNA is extracted therefrom, (c) the extracted DNA is primed with at least one, and preferably two, primers of the invention and amplified by polymerase chain reaction, and (d) the amplified DNA fragment is produced.

It is apparent that disclosure of polynucleotide sequences of SEQ ID No:1, its homologs and partial sequences enable their corresponding amino acid sequences. Accordingly, a sixth aspect of the invention features a substantially purified polypeptide or polypeptide derivative having an amino acid sequence encoded by a polynucleotide of the invention.

A "substantially purified polypeptide" as used herein is defined as a polypeptide that is separated from the environment in which it naturally occurs and/or that is free of the majority of the polypeptides that are present in the environment in which it was synthesized. For example, a substantially purified polypeptide is free from cytoplasmic polypeptides. Those skilled in the art would readily understand that the polypeptides of the invention may be purified from a natural source, i.e., a *Chlamydia* strain, or produced by recombinant means.

Consistent with the sixth aspect of the invention are polypeptides, homologs or fragments which are modified or treated to enhance their immunogenicity in the target animal, in whom the polypeptide, homolog or fragments are intended to confer protection against *Chlamydia*. Such modifications or treatments include: amino acid substitutions with an amino acid derivative such as 3-methyhistidine, 4-hydroxyproline, 5-hydroxylysine etc., modifications or deletions which are carried out after preparation of the polypeptide, homolog or fragment, such as the modification of free amino, carboxyl or hydroxyl side groups of the amino acids.

Identification of homologous polypeptides or polypeptide derivatives encoded by polynucleotides of the invention which have specific antigenicity is achieved by screening for cross-reactivity with an antiserum raised against the polypeptide of reference having an amino acid sequence of SEQ ID No:1. The procedure is as follows: a monospecific hyperimmune antiserum is raised against a purified reference polypeptide, a fusion polypeptide (for example, an expression product of MBP, GST, or His-tag systems, the description and instructions for use of which are contained in Invitrogen product manuals for pcDNA3.1/Myc-His(+) A, B, and C and for the Xpress™ System Protein Purification), or a synthetic peptide predicted to be antigenic. Where an antiserum is raised against a fusion polypeptide, two different fusion systems are employed. Specific antigenicity can be determined according to a number of methods, including Western blot (Towbin et al., Proc. Natl. Acad. Sci. USA (1979) 76:4350), dot blot, and ELISA, as described below.

In a Western blot assay, the product to be screened, either as a purified preparation or a total *E. coli* extract, is submitted to SDS-Page electrophoresis as described by Laemmli (Nature (1970) 227:680). After transfer to a nitrocellulose membrane, the material is further incubated with the monospecific hyperimmune antiserum diluted in the range of dilutions from about 1:5 to about 1:5000, preferably from about 1:100 to about 1:500. Specific antigenicity is shown once a band corresponding to the product exhibits reactivity at any of the dilutions in the above range.

In an ELISA assay, the product to be screened is preferably used as the coating antigen. A purified preparation is preferred, although a whole cell extract can also be used. Briefly, about 100 µl of a preparation at about 10 µg protein/ml are distributed into wells of a 96-well polycarbonate ELISA plate. The plate is incubated for 2 hours at 37° C. then overnight at 4° C. The plate is washed with phosphate buffer saline (PBS) containing 0.05% Tween 20 (PBS/Tween buffer). The wells are saturated with 250 µl PBS containing 1% bovine serum albumin (BSA) to prevent non-specific antibody binding. After 1 hour incubation at 37° C., the plate is washed with PBS/Tween buffer. The antiserum is serially diluted in PBS/Tween buffer containing 0.5% BSA. 100 µl of dilutions are added per well. The plate is incubated for 90 minutes at 37° C., washed and evaluated according to standard procedures. For example, a goat anti-rabbit peroxidase conjugate is added to the wells when specific antibodies were raised in rabbits. Incubation is carried out for 90 minutes at 37° C. and the plate is washed. The reaction is developed with the appropriate substrate and the reaction is measured by colorimetry (absorbance measured spectrophotometrically). Under the above experimental conditions, a positive reaction is shown by O.D. values greater than a non immune control serum.

In a dot blot assay, a purified product is preferred, although a whole cell extract can also be used. Briefly, a solution of the product at about 100 µg/ml is serially two-fold diluted in 50 mM Tris-HCl (pH 7.5). 100 µl of each dilution are applied to a nitrocellulose membrane 0.45 µm set in a 96-well dot blot apparatus (Biorad). The buffer is removed by applying vacuum to the system. Wells are washed by addition of 50 mM Tris-HCl (pH 7.5) and the membrane is air-dried. The membrane is saturated in blocking buffer (50 mM Tris-HCl (pH 7.5) 0.15 M NaCl, 10 g/L skim milk) and incubated with an antiserum dilution from about 1:50 to about 1:5000, preferably about 1:500. The reaction is revealed according to standard procedures. For example, a goat anti-rabbit peroxidase conjugate is added to the wells when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry. Under the above experimental conditions, a positive reaction is shown once a colored spot is associated with a dilution of at least about 1:5, preferably of at least about 1:500.

Therapeutic or prophylactic efficacy of a polypeptide or derivative of the invention can be evaluated as described below. A seventh aspect of the invention provides (i) a composition of matter comprising a polypeptide of the invention together with a diluent or carrier; specifically (ii) a pharmaceutical composition containing a therapeutically or prophylactically effective amount of a polypeptide of the invention; (iii) a method for inducing an immune response against *Chlamydia* in a mammal, by administering to the mammal an immunogenically effective amount of a polypeptide of the invention to elicit a protective immune response to *Chlamydia*; and particularly, (iv) a method for preventing and/or treating a *Chlamydia* (e.g., *C. trachomatis. C. psittaci, C. pneumoniae.* or *C. pecorum*) infection, by administering a prophylactic or therapeutic amount of a polypeptide of the invention to an infected individual. Additionally, the seventh aspect of the invention encompasses the use of a polypeptide of the invention in the preparation of a medicament for preventing and/or treating *Chlamydia* infection.

As used herein, the immunogenic compositions of the invention are administered by conventional routes known the vaccine field, in particular to a mucosal (e.g., ocular, intranasal, pulmonary, oral, gastric, intestinal, rectal, vaginal, or urinary tract) surface or via the parenteral (e.g., subcutaneous, intradermal, intramuscular, intravenous, or intraperitoneal) route. The choice of administration route depends upon a number of parameters, such as the adjuvant associated with the polypeptide. If a mucosal adjuvant is used, the intranasal or oral route is preferred. If a lipid formulation or an aluminum compound is used, the parenteral route is preferred with the sub-cutaneous or intramuscular route being most preferred. The choice also depends upon the nature of the vaccine agent. For example, a polypeptide of the invention fused to CTB or LTB is best administered to a mucosal surface.

As used herein, the composition of the invention contains one or several polypeptides or derivatives of the invention. The composition optionally contains at least one additional *Chlamydia* antigen, or a subunit, fragment, homolog, mutant, or derivative thereof.

For use in a composition of the invention, a polypeptide or derivative thereof is formulated into or with liposomes, preferably neutral or anionic liposomes, microspheres, ISCOMS, or virus-like-particles (VLPs) to facilitate delivery and/or enhance the immune response. These compounds are readily available to one skilled in the art; for example, see Liposomes: A Practical Approach, RCP New Ed, IRL press (1990).

Adjuvants other than liposomes and the like are also used and are known in the art. Adjuvants may protect the antigen from rapid dispersal by sequestering it in a local deposit, or they may contain substances that stimulate the host to secrete factors that are chemotactic for macrophages and other components of the immune system. An appropriate selection can conventionally be made by those skilled in the art, for example, from those described below (under the eleventh aspect of the invention).

Treatment is achieved in a single dose or repeated as necessary at intervals, as can be determined readily by one skilled in the art. For example, a priming dose is followed by three booster doses at weekly or monthly intervals. An appropriate dose depends on various parameters including the recipient (e.g., adult or infant), the particular vaccine antigen, the route and frequency of administration, the presence/absence or type of adjuvant, and the desired effect (e.g., protection and/or treatment), as can be determined by one skilled in the art. In general, a vaccine antigen of the invention is administered by a mucosal route in an amount from about 10 μg to about 500 mg, preferably from about 1 mg to about 200 mg. For the parenteral route of administration, the dose usually does not exceed about 1 mg, preferably about 100 μg.

When used as vaccine agents, polynucleotides and polypeptides of the invention may be used sequentially as part of a multistep immunization process. For example, a mammal is initially primed with a vaccine vector of the invention such as a pox virus, e.g., via the parenteral route, and then boosted twice with the polypeptide encoded by the vaccine vector, e.g., via the mucosal route. In another example, liposomes associated with a polypeptide or derivative of the invention is also used for priming, with boosting being carried out mucosally using a soluble polypeptide or derivative of the invention in combination with a mucosal adjuvant (e.g., LT).

A polypeptide derivative of the invention is also used in accordance with the seventh aspect as a diagnostic reagent for detecting the presence of anti-*Chlamydia* antibodies, e.g., in a blood sample. Such polypeptides are about 5 to about 80, preferably about 10 to about 50 amino acids in length. They are either labeled or unlabeled, depending upon the diagnostic method. Diagnostic methods involving such a reagent are described below.

Upon expression of a DNA molecule of the invention, a polypeptide or polypeptide derivative is produced and purified using known laboratory techniques. As described above, the polypeptide or polypeptide derivative may be produced as a fusion protein containing a fused tail that facilitates purification. The fusion product is used to immunize a small mammal, e.g., a mouse or a rabbit, in order to raise antibodies against the polypeptide or polypeptide derivative (monospecific antibodies). Accordingly, an eighth aspect of the invention provides a monospecific antibody that binds to a polypeptide or polypeptide derivative of the invention.

By "monospecific antibody" is meant an antibody that is capable of reacting with a unique naturally-occurring *Chlamydia* polypeptide. An antibody of the invention is either polyclonal or monoclonal. Monospecific antibodies may be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies may also be in the form of immunoglobulin fragments, e.g., F(ab)'2 or Fab fragments. The antibodies of the invention are of any isotype, e.g., IgG or IgA, and polyclonal antibodies are of a single isotype or a mixture of isotypes.

Antibodies against the polypeptides, homologs or fragments of the present invention are generated by immunization of a mammal with a composition comprising said polypeptide, homolog or fragment. Such antibodies may be polyclonal or monoclonal. Methods to produce polyclonal or monoclonal antibodies are well known in the art. For a review, see "Antibodies, A Laboratory Manual, Cold Spring Harbor Laboratory, Eds. E. Harlow and D. Lane (1988), and D. E. Yelton et al., 1981. Ann. Rev. Biochem. 50:657–680. For monoclonal antibodies, see Kohler & Milstein (1975) Nature 256:495–497.

The antibodies of the invention, which are raised to a polypeptide or polypeptide derivative of the invention, are produced and identified using standard immunological assays, e.g., Western blot analysis, dot blot assay, or ELISA (see, e.g., Coligan et al., Current Protocols in Immunology (1994) John Wiley & Sons, Inc., New York, N.Y.). The antibodies are used in diagnostic methods to detect the presence of a *Chlamydia* antigen in a sample, such as a biological sample. The antibodies are also used in affinity chromatography for purifying a polypeptide or polypeptide derivative of the invention. As is discussed further below, such antibodies may be used in prophylactic and therapeutic passive immunization methods.

Accordingly, a ninth aspect of the invention provides (i) a reagent for detecting the presence of *Chlamydia* in a biological sample that contains an antibody, polypeptide, or polypeptide derivative of the invention; and (ii) a diagnostic method for detecting the presence of *Chlamydia* in a biological sample, by contacting the biological sample with an antibody, a polypeptide, or a polypeptide derivative of the invention, such that an immune complex is formed, and by detecting such complex to indicate the presence of *Chlamydia* in the sample or the organism from which the sample is derived.

Those skilled in the art will readily understand that the immune complex is formed between a component of the sample and the antibody, polypeptide, or polypeptide derivative, whichever is used, and that any unbound material is removed prior to detecting the complex. It is understood that a polypeptide reagent is useful for detecting the presence of anti-*Chlamydia* antibodies in a sample, e.g., a blood sample, while an antibody of the invention is used for screening a sample, such as a gastric extract or biopsy, for the presence of *Chlamydia* polypeptides.

For diagnostic applications, the reagent (i.e., the antibody, polypeptide, or polypeptide derivative of the invention) is either in a free state or immobilized on a solid support, such as a tube, a bead, or any other conventional support used in the field. Immobilization is achieved using direct or indirect means. Direct means include passive adsorption (non-covalent binding) or covalent binding between the support and the reagent. By "indirect means" is meant that an anti-reagent compound that interacts with a reagent is first attached to the solid support. For example, if a polypeptide reagent is used, an antibody that binds to it can serve as an anti-reagent, provided that it binds to an epitope that is not involved in the recognition of antibodies in biological samples. Indirect means may also employ a ligand-receptor system, for example, where a molecule such as a vitamin is grafted onto the polypeptide reagent and the corresponding receptor immobilized on the solid phase. This is illustrated by the biotin-streptavidin system. Alternatively, a peptide tail is added chemically or by genetic engineering to the reagent and the grafted or fused product immobilized by passive adsorption or covalent linkage of the peptide tail.

Such diagnostic agents may be included in a kit which also comprises instructions for use. The reagent is labeled with a detection means which allows for the detection of the reagent when it is bound to its target. The detection means may be a fluorescent agent such as fluorescein isocyanate or fluorescein isothiocyanate, or an enzyme such as horse radish peroxidase or luciferase or alkaline phosphatase, or a radioactive element such as $^{125}$I or $^{51}$Cr.

Accordingly, a tenth aspect of the invention provides a process for purifying, from a biological sample, a polypeptide or polypeptide derivative of the invention, which involves carrying out antibody-based affinity chromatography with the biological sample, wherein the antibody is a monospecific antibody of the invention.

For use in a purification process of the invention, the antibody is either polyclonal or monospecific, and preferably is of the IgG type. Purified IgGs is prepared from an antiserum using standard methods (see, e.g., Coligan et al., Current Protocols in Immunology (1994) John Wiley & Sons, Inc., New York, N.Y.). Conventional chromatography supports, as well as standard methods for grafting antibodies, are described in, e.g., Antibodies: A Laboratory Manual, D. Lane, E. Harlow, Eds. (1988) and outlined below.

Briefly, a biological sample, such as an C. pneumoniae extract preferably in a buffer solution, is applied to a chromatography material, preferably equilibrated with the buffer used to dilute the biological sample so that the polypeptide or polypeptide derivative of the invention (i.e., the antigen) is allowed to adsorb onto the material. The chromatography material, such as a gel or a resin coupled to an antibody of the invention, is in either a batch form or a column. The unbound components are washed off and the antigen is then eluted with an appropriate elution buffer, such as a glycine buffer or a buffer containing a chaotropic agent, e.g., guanidine HCl, or high salt concentration (e.g., 3 M MgCl$_2$). Eluted fractions are recovered and the presence of the antigen is detected, e.g., by measuring the absorbance at 280 nm.

An eleventh aspect of the invention provides (i) a composition of matter comprising a monospecific antibody of the invention, together with a diluent or carrier; (ii) a pharmaceutical composition comprising a therapeutically or prophylactically effective amount of a monospecific antibody of the invention, and (iii) a method for treating or preventing a Chlamydia (e.g., C. trachomatis, C. psittaci, C. pneumoniae or C. pecorum) infection, by administering a therapeutic or prophylactic amount of a monospecific antibody of the invention to an infected individual. Additionally, the eleventh aspect of the invention encompasses the use of a monospecific antibody of the invention in the preparation of a medicament for treating or preventing Chlamydia infection.

The monospecific antibody is either polyclonal or monoclonal, preferably of the IgA isotype (predominantly). In passive immunization, the antibody is administered to a mucosal surface of a mammal, e.g., the gastric mucosa, e.g., orally or intragastrically, advantageously, in the presence of a bicarbonate buffer. Alternatively, systemic administration, not requiring a bicarbonate buffer, is carried out. A monospecific antibody of the invention is administered as a single active component or as a mixture with at least one monospecific antibody specific for a different Chlamydia polypeptide. The amount of antibody and the particular regimen used are readily determined by one skilled in the art. For example, daily administration of about 100 to 1,000 mg of antibodies over one week, or three doses per day of about 100 to 1,000 mg of antibodies over two or three days, are effective regimens for most purposes.

Therapeutic or prophylactic efficacy are evaluated using standard methods in the art, e.g., by measuring induction of a mucosal immune response or induction of protective and/or therapeutic immunity, using, e.g., the C. pneumoniae mouse model. Those skilled in the art will readily recognize that the C. pneumoniae strain of the model may be replaced with another Chlamydia strain. For example, the efficacy of DNA molecules and polypeptides from C. pneumoniae is preferably evaluated in a mouse model using C. pneumoniae strain. Protection is determined by comparing the degree of Chlamydia infection to that of a control group. Protection is shown when infection is reduced by comparison to the control group. Such an evaluation is made for polynucleotides, vaccine vectors, polypeptides and derivatives thereof, as well as antibodies of the invention.

Adjuvants useful in any of the vaccine compositions described above are as follows.

Adjuvants for parenteral administration include aluminum compounds, such as aluminum hydroxide, aluminum phosphate, and aluminum hydroxy phosphate. The antigen is precipitated with, or adsorbed onto, the aluminum compound according to standard protocols. Other adjuvants, such as RIBI (ImmunoChem, Hamilton, Mont.), are used in parenteral administration.

Adjuvants for mucosal administration include bacterial toxins, e.g., the cholera toxin (CT), the E. coli heat-labile toxin (LT), the Clostridium difficile toxin A and the pertussis toxin (PT), or combinations, subunits, toxoids, or mutants thereof such as a purified preparation of native cholera toxin subunit B (CTB). Fragments, homologs, derivatives, and fusions to any of these toxins are also suitable, provided that they retain adjuvant activity. Preferably, a mutant having reduced toxicity is used. Suitable mutants are described, e.g., in WO 95/17211 (Arg-7-Lys CT mutant), WO 96/06627 (Arg-192-Gly LT mutant), and WO 95/34323 (Arg-9-Lys and Glu-129-Gly PT mutant). Additional LT mutants that are used in the methods and compositions of the invention include, e.g., Ser-63-Lys, Ala-69-Gly, Glu-110-Asp, and Glu-112-Asp mutants. Other adjuvants, such as a bacterial monophosphoryl lipid A (MPLA) of, e.g., E. coli, Salmonella minnesota, Salmonella typhimurium, or Shigella flexneri; saponins, or polylactide glycolide (PLGA) microspheres, is also be used in mucosal administration.

Adjuvants useful for both mucosal and parenteral administrations include polyphosphazene (WO 95/02415), DC-chol (3 b-(N-(N',N'-dimethyl aminomethane)-carbamoyl) cholesterol; U.S. Pat. No. 5,283,185 and WO 96/14831) and QS-21 (WO 88/09336).

Any pharmaceutical composition of the invention containing a polynucleotide, a polypeptide, a polypeptide derivative, or an antibody of the invention, is manufactured in a conventional manner. In particular, it is formulated with a pharmaceutically acceptable diluent or carrier, e.g., water or a saline solution such as phosphate buffer saline. In general, a diluent or carrier is selected on the basis of the mode and route of administration, and standard pharmaceutical practice. Suitable pharmaceutical carriers or diluents, as well as pharmaceutical necessities for their use in pharmaceutical formulations, are described in *Remington's Pharmaceutical Sciences*, a standard reference text in this field and in the USP/NF.

The invention also includes methods in which *Chlamydia* infection are treated by oral administration of a *Chlamydia* polypeptide of the invention and a mucosal adjuvant, in combination with an antibiotic, an antacid, sucralfate, or a combination thereof. Examples of such compounds that can be administered with the vaccine antigen and the adjuvant are antibiotics, including, e.g., macrolides, tetracyclines, and derivatives thereof (specific examples of antibiotics that can be used include azithromycin or doxicyclin or immunomodulators such as cytokines or steroids). In addition, compounds containing more than one of the above-listed components coupled together, are used. The invention also includes compositions for carrying out these methods, i.e., compositions containing a *Chlamydia* antigen (or antigens) of the invention, an adjuvant, and one or more of the above-listed compounds, in a pharmaceutically acceptable carrier or diluent.

It has recently been shown that the 60 kDa cysteine rich membrane protein contains a sequence cross-reactive with the murine alpha-myosin heavy chain epitope M7A-alpha, an epitope conserved in humans (Bachmaier et al., Science (1999) 283:1335). This cross-reactivity is proposed to contribute to the development of cardiovascular disease, so it may be beneficial to remove this epitope, and any other epitopes cross-reactive with human antigens, from the protein if it is to be used as a vaccine. Accordingly, a further embodiment of the present invention includes the modification of the coding sequence, for example, by deletion or substitution of the nucleotides encoding the epitope from polynucleotides encoding the protein, as to improve the efficacy and safety of the protein as a vaccine. A similar approach may be appropriate for any protective antigen found to have unwanted homologies or cross-reactivities with human antigens.

Amounts of the above-listed compounds used in the methods and compositions of the invention are readily determined by one skilled in the art. Treatment/immunization schedules are also known and readily designed by one skilled in the art. For example, the non-vaccine components can be administered on days 1–14, and the vaccine antigen+adjuvant can be administered on days 7, 14, 21, and 28.

EXAMPLES

The above disclosure generally discribes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Example 1

This example illustrates the preparation of a plasmid vector pCACRMP60 containing the 60 kDa cysteine rich membrane protein gene.

The 60 kDa cysteine rich membrane protein gene was amplified from *Chlamydia pneumoniae* genomic DNA by polymerase chain reaction (PCR) using a 5' primer (5' ATAAGAATGCGGCCGCCACCATGTCCAAACTCATCAGACGAGTAG 3')(SEQ ID No:3) and a 3' primer (5' GCGCCGGATCCGATACACGTGGGTATTTTCTGTG 3') (SEQ ID No:4). The 5' primer contains a Not I restriction site, a ribosome binding site, an initiation codon and a sequence at the 5' end of the 60 kDa cysteine rich membrane protein coding sequence. The 3' primer includes the sequence encoding the C-terminal sequence of the 60 kDa cysteine rich membrane protein and a Bam HI restriction site. The stop codon was excluded and an additional nucleotide was inserted to obtain an in-frame fusion with the Histidine tag.

After amplification, the PCR fragment was purified using QIAquick™ PCR purification kit (Qiagen) and then digested with Not I and Bam HI and cloned into the pCA-Myc-His eukaryotic expression vector describe in example 2 (FIG. 3) with transcription under control of the human CMV promoter.

Example 2

This example illustrates the preparation of the eukaryotic expression vector pCA/Myc-His.

Plasmid pcDNA3.1(−)Myc-His C (Invitrogen) was restricted with Spe I and Bam HI to remove the CMV promoter and the remaining vector fragment was isolated. The CMV promoter and intron A from plasmid VR-1012 (Vical) was isolated on a Spe I/Bam HI fragment. The fragments were ligated together to produce plasmid pCA/Myc-His. The Not I/Bam HI restricted PCR fragment containing the 60 kDa cysteine rich membrane protein gene was ligated into the Not I and Bam HI restricted plasmid pCA/Myc-His to produce plasmid pCACRMP60 (FIG. 3).

The resulting plasmid, pCACRMP60, was transferred by electroporation into *E. coli* XL-1 blue (Stratagene) which was grown in LB broth containing 50 μg/ml of carbenicillin. The plasmid was isolated by Endo Free Plasmid Giga Kit™ (Qiagen) large scale DNA purification system. DNA concentration was determined by absorbance at 260 nm and the plasmid was verified after gel electrophoresis and Ethidium bromide staining and comparison to molecular weight standards. The 5' and 3' ends of the gene were verified by sequencing using a LiCor model 4000 L DNA sequencer and IRD-800 labelled primers.

Example 3

This example illustrates the immunization of mice to achieve protection against an intranasal challenge of *C. pneumoniae.*

It has been previously demonstrated (Yang et. al., 1993) that mice are susceptible to intranasal infection with different isolates of *C. pneumoniae*. Strain AR-39 (Grayston, 1989) was used in Balb/c mice as a challenge infection model to examine the capacity of chlamydia gene products delivered as naked DNA to elicit a protective response against a sublethal *C. pneumoniae* lung infection. Protective immunity is defined as an accelerated clearance of pulmonary infection.

Groups of 7 to 9 week old male Balb/c mice (8 to 10 per group) were immunized intramuscularly (i.m.) plus intranasally (i.n.) with plasmid DNA containing the coding sequence of *C. pneumoniae* 60 kDa cysteine rich membrane protein as described in Example 1 and 2. Saline or the plasmid vector lacking an inserted chlamydial gene was given to groups of control animals.

For i.m. immunization alternate left and right quadriceps were injected with 100 μg of DNA in 50 μl of PBS on three occasions at 0, 3 and 6 weeks. For i.n. immunization, anaesthetized mice aspirated 50 μl of PBS containing 50 μg DNA on three occasions at 0, 3 and 6 weeks. At week 8, immunized mice were inoculated i.n. with 5×10⁵ IFU of *C. pneumoniae*, strain AR39 in 100 μl of SPG buffer to test their ability to limit the growth of a sublethal *C. pneumoniae* challenge.

Lungs were taken from mice at days 5 and 9 post-challenge and immediately homogenised in SPG buffer (7.5% sucrose, 5 mM glutamate, 12.5 mM phosphate pH7.5). The homogenate was stored frozen at −70° C. until assay. Dilutions of the homogenate were assayed for the presence of infectious *chlamydia* by inoculation onto monolayers of susceptible cells. The inoculum was centrifuged onto the cells at 3000 rpm for 1 hour, then the cells were incubated for three days at 35° C. in the presence of 1 μg/ml cycloheximide. After incubation the monolayers were fixed with formalin and methanol then immunoperoxidase stained for the presence of chlamydial inclusions using convalescent sera from rabbits infected with *C. pneumoniae* and metal-enhanced DAB as a peroxidase substrate.

FIG. 4 and Table 1 show that mice immunized i.n. and i.m. with pCACRMP60 had chlamydial lung titers less than 1400 in 4 of 4 cases at day 5 and less than 400 in 4 of 4 cases at day 9 whereas the range of values for control mice sham immunized with saline was 1200–2100 IFU/lung (mean 1680) at day 5 and 1100–12400 IFU/lung (mean 4320) at day 9. DNA immunisation per se was not responsible for the observed protective effect since another plasmid DNA construct, pCAI422, failed to protect, with lung titers in immunised mice similar to those obtained for saline-immunized control mice. The construct pCAI422 is identical to pCACRMP60 except that the nucleotide sequence encoding the 60 kDa cysteine rich membrane protein is replaced with a *C. pneumoniae* nucleotide sequence encoding a non-protective protein.

TABLE 1

BACTERIAL LOAD (INCLUSION FORMING UNITS PER LUNG) IN THE LUNGS OF BALB/C MICE IMMUNIZED WITH VARIOUS DNA IMMUNIZATION CONSTRUCTS

| MOUSE | Saline Day 5 | Saline Day 9 | pCACRMP60 Day 5 | pCACRMP60 Day 9 | pCA1422 Day 5 | pCA1422 Day 9 |
|---|---|---|---|---|---|---|
| 1 | 1800 | 1100 | 200 | 300 | 2200 | 3100 |
| 2 | 1200 | 2100 | 100 | 0 | 1300 | 8100 |
| 3 | 2100 | 12400 | 500 | 200 | 700 | 500 |
| 4 | 1900 | 3900 | 1300 | 0 | 1000 | 1400 |
| 5 | 1400 | 2100 | | | | |
| MEAN | 1680 | 4320 | 525 | 125 | 1300 | 3275 |
| SD | 370.14 | 4628.39 | 543.9056 | 150.00 | 648.07 | 3392.52 |

The invention claimed is:

1. A vaccine vector comprising an isolated nucleic acid molecule operably linked to a promoter functional in a mammalian cell, wherein the nucleic acid molecule encodes a polypeptide selected from any of:
   (a) SEQ ID No:2;
   (b) an immunogenic fragment consisting of at least 50 consecutive amino acids from SEQ ID No:2; and
   (c) a polypeptide which has been modified without loss of immunogenicity,
wherein said modified polypeptide is at least 95% identical in amino acid sequence to SEQ ID NO:2;
wherein the polypeptide, when used to immunize an animal, confers immunoprotection to the animal against *Chlamydia*.

2. The vaccine vector of claim 1 further comprising another nucleic acid encoding an additional polypeptide which enhances the immune response to the polypeptide having SEQ ID No: 2, wherein the additional polypeptide is a *Chlamydia* polypeptide.

3. The vaccine vector of claim 1 wherein the promoter is a viral promoter.

4. The vaccine vector of claim 1 wherein the nucleic acid molecule encodes SEQ ID No:2.

5. The vaccine vector of claim 4 wherein the promoter is a viral promoter.

6. The vaccine vector of claim 3 wherein the promoter is cytomegalovirus (CMV) promoter.

7. The vaccine vector of claim 5 wherein the promoter is cytomegalovirus (CMV) promoter.

8. The vaccine vector of claim 1 wherein the nucleic acid molecule encodes an immunogenic fragment consisting of at least 50 consecutive amino acids from SEQ ID No:2.

9. The vaccine vector of claim 1 wherein the nucleic acid molecule encodes a polypeptide which has been modified without loss of immunogenicity, wherein said modified polypeptide is at least 95% identical in amino acid sequence to SEQ ID NO:2.

10. The vaccine vector of claim 8 wherein the promoter is a viral promoter.

11. The vaccine vector of claim 9 wherein the promoter is a viral promoter.

12. The vaccine vector of claim 1 comprising the nucleotide sequence set forth in SEQ ID No:1 operably linked to a promoter functional in a mammalian cell.

13. A vaccine comprising the vaccine vector according to claim 1 and a pharmaceutically acceptable carrier.

14. A vaccine comprising the vaccine vector according to claim 9 and a pharmaceutically acceptable carrier.

15. A vaccine comprising the vaccine vector according to claim 3 and a pharmaceutically acceptable carrier.

16. A vaccine comprising the vaccine vector according to claim 5 and a pharmaceutically acceptable carrier.

17. A vaccine comprising the vaccine vector according to claim 6 and a pharmaceutically acceptable carrier.

18. A vaccine comprising the vaccine vector according to claim 7 and a pharmaceutically acceptable carrier.

19. A vaccine comprising the vaccine vector according to claim 4 and a pharmaceutically acceptable carrier.

20. A vaccine comprising the vaccine vector according to claim 8 and a pharmaceutically acceptable carrier.

21. A vaccine comprising the vaccine vector according to claim 1 and an adjuvant.

22. A vaccine comprising the vaccine vector according to claim 9 and an adjuvant.

23. A vaccine comprising the vaccine vector according to claim 3 and an adjuvant.

24. A vaccine comprising the vaccine vector according to claim 6 and an adjuvant.

25. The vaccine vector according to claim 1 in unit dosage form.

26. The vaccine vector according to claim 9 in unit dosage form.

27. The vaccine vector according to claim 3 in unit dosage form.

28. The vaccine vector according to claim 6 in unit dosage form.

29. The vaccine vector according to claim 1 which is unable to replicate in mammalian cells and unable to integrate in a mammalian genome.

30. The vaccine vector according to claim 9 which is unable to replicate in mammalian cells and unable to integrate in a mammalian genome.

31. The vaccine vector according to claim 3 which is unable to replicate in mammalian cells and unable to integrate in a mammalian genome.

32. The vaccine vector according to claim 6 which is unable to replicate in mammalian cells and unable to integrate in a mammalian genome.

33. The vaccine vector according to claim 1 which, when used to immunize mice, reduces Chlamydial lung titer by at least 50% at 5 days post-challenge in mice intranasally infected with *C. pneumoniae*, compared to mice not immunized with the vaccine vector.

34. The vaccine vector according to claim 9 which, when used to immunize mice, reduces Chlamydial lung titer by at least 50% at 5 days post-challenge in mice intranasally infected with *C. pneumoniae*, compared to mice not immunized with the vaccine vector.

35. The vaccine vector according to claim 3 which, when used to immunize mice, reduces Chlamydial lung titer by at least 50% at 5 days post-challenge in mice intranasally infected with *C. pneumoniae*, compared to mice not immunized with the vaccine vector.

36. The vaccine vector according to claim 6 which, when used to immunize mice, reduces Chlamydial lung titer by at least 50% at 5 days post-challenge in mice intranasally infected with *C. pneumoniae*, compared to mice not immunized with the vaccine vector.

* * * * *